US011147591B2

(12) United States Patent
Jackson

(10) Patent No.: US 11,147,591 B2
(45) **Date of Patent: *Oct. 19, 2021**

(54) PIVOTAL BONE ANCHOR RECEIVER ASSEMBLY WITH THREADED CLOSURE

(71) Applicant: Roger P Jackson, Prairie Village, KS (US)

(72) Inventor: Roger P Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/612,906

(22) Filed: Feb. 3, 2015

(65) Prior Publication Data

US 2015/0148846 A1 May 28, 2015

Related U.S. Application Data

(63) Continuation of application No. 13/896,490, filed on May 17, 2013, now Pat. No. 8,998,960, which is a continuation of application No. 12/807,937, filed on Sep. 17, 2010, now Pat. No. 8,444,677, which is a continuation of application No. 10/986,377, filed on Nov. 10, 2004, now Pat. No. 7,833,250.

(51) Int. Cl.
*A61B 17/70* (2006.01)

(52) U.S. Cl.
CPC ...... *A61B 17/7032* (2013.01); *A61B 17/7037* (2013.01); *A61B 17/7011* (2013.01)

(58) Field of Classification Search
CPC ........................ A61B 17/7035; A61B 17/7082
USPC .......................................................... 606/270
See application file for complete search history.

(56) References Cited

U.S. PATENT DOCUMENTS

| | | | | |
|---|---|---|---|---|
| 154,864 A | | 9/1874 | Harvey | |
| 447,775 A | | 3/1891 | Higbee | |
| 791,548 A | | 6/1905 | Fischer | |
| 1,300,275 A | | 4/1919 | Johnson | |
| 1,330,673 A | | 2/1920 | Anderson | |
| 1,472,464 A | | 10/1923 | Ellison | |
| 2,005,348 A | | 6/1935 | Michell | |
| 2,083,092 A | | 6/1937 | Richer | |
| 2,201,087 A | | 5/1940 | Hallowell | |
| 2,239,352 A | | 4/1941 | Cherry | |
| 2,243,717 A | | 5/1941 | Moreira | |
| 2,244,046 A | * | 6/1941 | Bradshaw | A47G 3/00 411/403 |
| 2,295,314 A | | 9/1942 | Whitney | |
| 2,346,346 A | | 4/1944 | Anderson | |

(Continued)

FOREIGN PATENT DOCUMENTS

| | | |
|---|---|---|
| AU | 2012203959 | 8/2012 |
| DE | 373809 | 4/1923 |

(Continued)

OTHER PUBLICATIONS

Brochure of Tyco/Healthcare/Surgical Dynamics on Spiral Radius 90D, Publication Date: Sep. 2001. pp. 1-8.

(Continued)

*Primary Examiner* — Anu Ramana
(74) *Attorney, Agent, or Firm* — Polsinelli PC

(57) ABSTRACT

A pivotal bone screw assembly includes a threaded shank body having an upper capture structure and a head. The head has a U-shaped cradle defining a channel for receiving a spinal fixation rod.

31 Claims, 9 Drawing Sheets

(56) References Cited

U.S. PATENT DOCUMENTS 2,362,999 A 11/1944 Elmer
2,445,978 A 7/1948 Stellin
2,531,892 A 11/1950 Reese
2,532,815 A 12/1950 Kindsvatter et al.
2,537,029 A 1/1951 Cambern
2,553,337 A 5/1951 Shafer
2,631,635 A 3/1953 Klooz
2,778,265 A 1/1957 Brown
2,813,450 A 11/1957 Dzus
2,833,325 A * 5/1958 Laisy ..................... F16B 35/06 411/260
2,877,681 A 3/1959 Brown
2,927,332 A 3/1960 Moore
2,969,250 A 1/1961 Kull
3,013,244 A 12/1961 Rudy
3,143,029 A 8/1964 Brown
D200,217 S 2/1965 Curtiss
3,236,275 A 2/1966 Smith
3,370,341 A 2/1968 Allsop
3,419,058 A 12/1968 Walker
3,444,775 A 5/1969 Hills
3,498,174 A 3/1970 Schuster et al.
3,584,667 A 6/1971 Reiland
3,604,487 A 9/1971 Gilbert
3,640,416 A 2/1972 Temple
3,664,440 A 5/1972 Elenburg
3,812,757 A 5/1974 Reiland
3,963,304 A 6/1976 Suzuki
3,963,322 A 6/1976 Gryctko
3,977,221 A 8/1976 Foote
3,990,671 A 9/1976 Seyler
3,989,284 A 11/1976 Blose
3,997,138 A 12/1976 Crock et al.
4,013,071 A 3/1977 Rosenberg
4,033,139 A 7/1977 Frederick
4,041,939 A 8/1977 Hall
4,103,422 A 8/1978 Weiss et al.
4,141,752 A 2/1979 Shipko
4,176,679 A 12/1979 Roger
4,190,091 A 2/1980 Colognori
4,199,216 A 4/1980 Gryctko
4,210,374 A 7/1980 Churla
4,269,246 A 5/1981 Larson et al.
4,304,424 A 12/1981 Hansen
4,323,326 A 4/1982 Okada et al.
4,347,845 A 9/1982 Mayfield
4,369,769 A 1/1983 Edwards
4,373,754 A 2/1983 Bollfrass et al.
4,409,968 A 10/1983 Drummond
4,448,191 A 5/1984 Rodnyansky et al.
4,472,005 A 9/1984 Norton
4,484,570 A 11/1984 Sutter et al.
4,492,500 A 1/1985 Ewing
4,506,917 A 3/1985 Hansen
4,528,874 A * 7/1985 Dunn .................... B25B 15/007 411/410
4,538,947 A 9/1985 Burkholder
4,577,448 A 3/1986 Howorth
4,600,224 A 7/1986 Blose
4,600,225 A 7/1986 Blose
4,627,759 A 12/1986 Kato
4,641,636 A 2/1987 Cotrel
4,653,481 A 3/1987 Howland et al.
4,653,486 A 3/1987 Coker
4,703,954 A 11/1987 Ortloff et al.
4,707,001 A 11/1987 Johnson
4,720,082 A 1/1988 Yang
4,743,260 A 5/1988 Burton
4,748,260 A 5/1988 Marlett
4,759,672 A 7/1988 Nilsen et al.
4,763,644 A 8/1988 Webb
4,764,068 A 8/1988 Crispell
4,790,297 A 12/1988 Luque
4,805,602 A 2/1989 Puno et al.
4,815,453 A 3/1989 Cotrel
4,836,196 A 6/1989 Park et al.
4,838,264 A 6/1989 Bremer et al.
4,850,775 A 7/1989 Lee et al.
4,877,020 A 10/1989 Vich
4,887,596 A 12/1989 Sherman
4,917,606 A 4/1990 Miller
D309,664 S 7/1990 McGrane
4,946,458 A 8/1990 Harms et al.
4,950,269 A 8/1990 Gaines, Jr.
4,961,740 A 10/1990 Ray et al.
5,005,562 A 4/1991 Cotrel
5,009,539 A 4/1991 Muellenberg
5,019,080 A 5/1991 Hemer
5,022,791 A 6/1991 Isler
5,024,213 A 6/1991 Asher et al.
5,025,676 A 6/1991 Perretta
5,034,011 A 7/1991 Howland
5,042,982 A 8/1991 Harms et al.
5,048,155 A 9/1991 Hwang
5,056,492 A 10/1991 Banse
5,067,428 A 11/1991 Dickerson et al.
5,067,955 A 11/1991 Cotrel
5,073,074 A 12/1991 Corrigan et al.
5,084,048 A 1/1992 Jacob et al.
5,092,635 A 3/1992 DeLange et al.
5,102,412 A 4/1992 Rogozinski
5,129,388 A 7/1992 Vignaud et al.
5,129,899 A 7/1992 Small et al.
5,129,900 A 7/1992 Asher et al.
5,147,360 A 9/1992 Dubousset
5,147,363 A 9/1992 Harle
5,154,719 A 10/1992 Cotrel
5,171,279 A * 12/1992 Mathews ............... A61B 17/70 128/898
5,176,483 A 1/1993 Baumann et al.
5,176,678 A 1/1993 Tsou
5,176,680 A 1/1993 Vignaud et al.
5,180,393 A 1/1993 Commarmond
5,201,678 A 4/1993 Venezia
5,201,734 A 4/1993 Cozad et al.
5,207,678 A 5/1993 Harms et al.
5,217,497 A 6/1993 Mehdian
5,224,596 A 7/1993 Kruger
5,234,430 A * 8/1993 Huebner ............ A61B 17/8645 606/318
5,244,323 A 9/1993 Tucchio
5,257,993 A 11/1993 Asher et al.
5,261,907 A 11/1993 Vignaud et al.
5,263,953 A 11/1993 Bagby
5,275,601 A 1/1994 Gogolewski et al.
5,282,707 A 2/1994 Palm
5,282,862 A 2/1994 Barker et al.
5,282,863 A 2/1994 Burton
D346,150 S 4/1994 Triantopoulos
5,306,275 A 4/1994 Bryan
5,312,404 A 5/1994 Asher et al.
5,321,901 A 6/1994 Kelly
5,330,472 A 7/1994 Metz-Stavenhagen
5,334,203 A 8/1994 Wagner
5,346,493 A 9/1994 Stahurski et al.
5,354,292 A 10/1994 Braeuer et al.
5,354,299 A 10/1994 Coleman
5,358,289 A 10/1994 Banker et al.
5,360,431 A 11/1994 Puno et al.
5,364,400 A 11/1994 Rego, Jr. et al.
5,366,330 A 11/1994 Cosenza
5,375,823 A 12/1994 Navas
5,382,248 A 1/1995 Jacobson et al.
5,385,583 A 1/1995 Cotrel
5,387,211 A 2/1995 Saadatmanesh et al.
5,387,212 A 2/1995 Yuan et al.
5,395,371 A 3/1995 Miller et al.
5,409,488 A 4/1995 Ulrich
5,409,489 A 4/1995 Sioufi
5,415,661 A 5/1995 Holmes
5,423,816 A 6/1995 Lin
5,427,418 A 6/1995 Watts
5,429,639 A 7/1995 Judet
5,431,651 A 7/1995 Goble

(56) References Cited

U.S. PATENT DOCUMENTS 5,434,001 A 7/1995 Yamada et al.
5,443,467 A 8/1995 Biedermann et al.
5,466,237 A 11/1995 Byrd, III et al.
5,466,238 A 11/1995 Lin
5,468,241 A 11/1995 Metz-Stavenhagen et al.
5,474,551 A 12/1995 Finn et al.
5,474,555 A 12/1995 Puno et al.
5,476,462 A 12/1995 Allard et al.
5,476,464 A 12/1995 Metz-Stavenhagen et al.
5,480,401 A 1/1996 Navas
5,484,440 A 1/1996 Allard
5,487,742 A 1/1996 Cotrel
5,487,744 A 1/1996 Howland
5,489,307 A 2/1996 Kuslich et al.
5,490,750 A 2/1996 Gundy
5,496,321 A 3/1996 Puno et al.
5,499,892 A 3/1996 Reed
5,501,684 A 3/1996 Schlapfer et al.
5,505,731 A 4/1996 Tornier
5,507,745 A 4/1996 Logroscino et al.
5,507,747 A 4/1996 Yuan et al.
5,520,454 A 5/1996 Laing
5,534,001 A 7/1996 Schlapfer et al.
5,540,688 A 7/1996 Navas
5,545,165 A 8/1996 Biedermann et al.
5,549,607 A 8/1996 Olson et al.
5,549,608 A 8/1996 Errico et al.
5,533,912 A 9/1996 Fillinger
5,554,157 A 9/1996 Errico et al.
5,562,660 A 10/1996 Grob
5,562,663 A 10/1996 Wisnewski et al.
5,569,247 A 10/1996 Morrison
5,569,251 A 10/1996 Baker et al.
5,578,033 A 11/1996 Errico et al.
5,584,834 A 12/1996 Errico et al.
5,586,984 A 12/1996 Errico et al.
5,591,166 A 1/1997 Bernhardt et al.
5,601,553 A 2/1997 Trebing et al.
5,605,458 A 2/1997 Bailey et al.
5,607,304 A 3/1997 Bailey et al.
5,607,425 A 3/1997 Rogozinski
5,607,426 A 3/1997 Ralph et al.
5,607,428 A 3/1997 Lin
5,609,593 A 3/1997 Errico et al.
5,609,594 A 3/1997 Errico et al.
5,611,800 A 3/1997 Davis et al.
5,628,740 A 5/1997 Mullane
5,630,817 A 5/1997 Rokegem
5,641,256 A 6/1997 Gundy
5,643,260 A 7/1997 Doherty
5,643,261 A 7/1997 Schaefer et al.
5,647,873 A 7/1997 Errico et al.
5,653,710 A 8/1997 Harle
5,662,650 A 9/1997 Bailey et al.
5,662,652 A 9/1997 Schaefer et al.
5,662,653 A 9/1997 Songer et al.
5,667,508 A 9/1997 Errico et al.
5,669,909 A 9/1997 Zdeblick et al.
5,669,911 A 9/1997 Errico et al.
5,672,175 A 9/1997 Martin
5,672,176 A 9/1997 Biedermann et al.
5,676,665 A 10/1997 Bryan
5,676,703 A 10/1997 Gelbard
5,681,319 A 10/1997 Biedermann et al.
5,683,390 A 11/1997 Metz-Stavenhagen et al.
5,683,391 A 11/1997 Boyd
5,690,630 A 11/1997 Errico et al.
5,697,929 A 12/1997 Mellinger
5,702,393 A 12/1997 Pfaifer
5,711,709 A 1/1998 McCoy
5,713,705 A 2/1998 Grunbichler
5,713,898 A 2/1998 Stuecker et al.
5,716,356 A 2/1998 Biedermann et al.
5,720,751 A 2/1998 Jackson
5,723,013 A 3/1998 Jeanson et al.
5,725,527 A 3/1998 Biedermann et al.
5,725,528 A 3/1998 Errico et al.
5,727,314 A 3/1998 Ashcraft
5,728,098 A 3/1998 Sherman et al.
5,733,286 A 3/1998 Errico et al.
5,738,685 A 4/1998 Halm et al.
5,741,254 A 4/1998 Henry et al.
5,752,957 A 5/1998 Ralph et al.
5,776,134 A 7/1998 Howland
5,782,833 A 7/1998 Haider
5,797,911 A 8/1998 Sherman et al.
5,800,435 A 9/1998 Errico et al.
5,800,547 A 9/1998 Schaefer et al.
5,817,094 A 10/1998 Errico et al.
5,848,913 A 12/1998 Ashcraft
5,863,293 A 1/1999 Richelsoph
5,870,934 A 2/1999 Cullinan
5,873,878 A 2/1999 Harms et al.
D407,302 S 3/1999 Lawson
5,876,402 A 3/1999 Errico et al.
5,879,350 A 3/1999 Sherman et al.
5,879,351 A 3/1999 Viart
5,882,350 A 3/1999 Ralph et al.
5,885,286 A 3/1999 Sherman et al.
5,902,303 A 5/1999 Eckhof et al.
RE36,221 E 6/1999 Breard et al.
5,910,141 A 6/1999 Morrison et al.
5,910,142 A 6/1999 Tatar
5,928,236 A 7/1999 Augagneur et al.
5,938,663 A 8/1999 Petreto
5,941,880 A 8/1999 Errico et al.
5,941,885 A 8/1999 Jackson
5,944,465 A 8/1999 Janitzki
5,951,553 A 9/1999 Betz et al.
5,954,725 A 9/1999 Sherman et al.
5,961,517 A 10/1999 Biedermann et al.
5,964,760 A 10/1999 Richelsoph
5,964,767 A 10/1999 Tapia et al.
5,997,539 A 12/1999 Errico et al.
6,001,098 A 12/1999 Metz-Stavenhagen et al.
6,004,349 A 12/1999 Jackson
6,006,930 A 12/1999 Dreyer et al.
6,010,502 A 1/2000 Bagby
6,010,503 A 1/2000 Richelsoph et al.
6,019,759 A 2/2000 Rogozinski
6,022,350 A 2/2000 Ganem
6,053,078 A 4/2000 Parker
6,053,917 A 4/2000 Sherman et al.
6,056,753 A 5/2000 Jackson
6,059,786 A 5/2000 Jackson
6,063,088 A 5/2000 Winslow
6,063,090 A 5/2000 Schlapler
6,074,147 A 6/2000 Shu
6,074,391 A 6/2000 Metz-Stavenhagen et al.
6,076,437 A 6/2000 Saint Martin
6,077,262 A 6/2000 Schlapfer et al.
6,077,267 A 6/2000 Huene
6,086,588 A 7/2000 Ameil et al.
6,090,110 A 7/2000 Metz-Stavenhagen
6,090,111 A 7/2000 Nichols
6,099,528 A 8/2000 Saurat
6,102,913 A 8/2000 Jackson
6,110,172 A 8/2000 Jackson
6,113,601 A 9/2000 Tatar
6,117,137 A 9/2000 Halm et al.
6,129,763 A 10/2000 Chauvin et al.
6,132,431 A 10/2000 Nilsson et al.
6,135,321 A 10/2000 Hippensteel
6,136,002 A 10/2000 Shih et al.
6,136,003 A 10/2000 Hoeck et al.
6,139,549 A 10/2000 Keller
6,143,032 A 11/2000 Schaefer et al.
6,146,383 A 11/2000 Studer et al.
6,149,533 A 11/2000 Finn
6,158,996 A 12/2000 Becher
6,162,223 A 12/2000 Orsak et al.
6,168,597 B1 1/2001 Biedermann et al.
6,179,841 B1 1/2001 Jackson
6,183,472 B1 2/2001 Lutz

(56) References Cited

U.S. PATENT DOCUMENTS 6,186,718 B1 2/2001 Fogard
6,193,719 B1 2/2001 Gournay
6,193,720 B1 2/2001 Yuan et al.
6,209,575 B1 4/2001 Graziano
6,214,012 B1 4/2001 Karpman et al.
RE37,161 E 5/2001 Michelson et al.
6,224,596 B1 5/2001 Jackson
6,224,598 B1 5/2001 Jackson
6,235,028 B1 5/2001 Brumfield et al.
6,235,034 B1 5/2001 Bray
6,241,730 B1 6/2001 Alby
6,241,731 B1 6/2001 Fiz
6,248,105 B1 6/2001 Schlapfer et al.
6,248,107 B1 6/2001 Foley et al.
6,251,112 B1 6/2001 Jackson
6,254,146 B1 7/2001 Church
6,254,602 B1 7/2001 Justis
6,261,039 B1 7/2001 Reed
6,261,288 B1 7/2001 Jackson
6,267,764 B1 7/2001 Elberg
6,267,765 B1 7/2001 Taylor et al.
6,280,442 B1 8/2001 Barker et al.
6,280,445 B1 8/2001 Morrison et al.
6,287,308 B1 9/2001 Betz et al.
6,296,642 B1 10/2001 Morrison et al.
6,296,643 B1 10/2001 Hopf et al.
6,299,613 B1 10/2001 Ogilvie et al.
6,299,616 B1 10/2001 Beger
6,302,888 B1 10/2001 Mellinger
6,309,391 B1 10/2001 Crandall et al.
6,315,564 B1 11/2001 Levisman
6,322,108 B1 11/2001 Riesselmann et al.
6,355,040 B1 3/2002 Richelsoph et al.
6,361,535 B2 3/2002 Jackson
RE37,665 E 4/2002 Ralph et al.
6,368,321 B1 4/2002 Jackson
6,371,957 B1 4/2002 Amrein et al.
6,379,356 B1 4/2002 Jackson
6,402,757 B1 6/2002 Moore et al.
6,412,831 B1 7/2002 Noel et al.
6,440,133 B1 8/2002 Beale et al.
6,440,137 B1 8/2002 Horvath et al.
6,443,953 B1 * 9/2002 Perra .................. A61B 17/7032
606/270
6,443,956 B1 9/2002 Ray
6,454,768 B1 9/2002 Jackson
6,454,772 B1 9/2002 Jackson
6,467,958 B1 10/2002 Sasaki et al.
6,471,703 B1 10/2002 Ashman
6,471,705 B1 10/2002 Biedermann et al.
6,478,795 B1 11/2002 Gournay
6,478,797 B1 11/2002 Paul
6,478,798 B1 11/2002 Howland
6,485,491 B1 11/2002 Farris et al.
6,485,492 B1 11/2002 Halm et al.
6,485,494 B1 11/2002 Haider
6,488,681 B2 12/2002 Martin et al.
6,520,962 B1 2/2003 Taylor et al.
6,527,804 B1 3/2003 Gauchet et al.
6,533,786 B1 3/2003 Needham et al.
6,550,959 B2 4/2003 Huber
6,554,831 B1 4/2003 Rivard et al.
6,554,834 B1 4/2003 Crozet et al.
6,562,040 B1 5/2003 Wagner
6,565,565 B1 5/2003 Yuan et al.
6,565,567 B1 5/2003 Haider
6,595,992 B1 7/2003 Wagner et al.
6,602,255 B1 8/2003 Campbell et al.
6,613,050 B1 9/2003 Wagner et al.
6,616,667 B1 9/2003 Steiger et al.
6,634,246 B2 10/2003 Ohya
6,634,842 B2 10/2003 Ueno
6,648,885 B1 11/2003 Friesem
6,648,888 B1 11/2003 Shluzas
6,652,526 B1 11/2003 Arafiles
6,652,765 B1 11/2003 Beaty
6,656,179 B1 12/2003 Schaefer et al.
6,663,632 B1 12/2003 Frigg
6,673,073 B1 1/2004 Schaefer
6,676,661 B1 1/2004 Benlloch et al.
6,688,921 B2 2/2004 Borgstrom
6,699,248 B2 3/2004 Jackson
6,712,818 B1 3/2004 Michelson
6,716,214 B1 4/2004 Jackson
6,730,089 B2 5/2004 Jackson
6,743,231 B1 6/2004 Gray et al.
6,755,829 B1 6/2004 Bono et al.
6,764,354 B2 7/2004 Kaine
6,778,861 B1 8/2004 Liebrecht et al.
6,783,527 B2 8/2004 Drewry et al.
6,786,903 B2 9/2004 Lin
6,788,756 B2 9/2004 Erbes
6,817,910 B2 11/2004 Borgstrom
6,835,196 B2 12/2004 Biedermann et al.
6,837,889 B2 1/2005 Shluzas
6,843,791 B2 1/2005 Serhan
6,851,337 B2 2/2005 Stokes
6,872,208 B1 3/2005 McBride et al.
6,896,677 B1 5/2005 Lin
6,899,714 B2 5/2005 Vaughan
6,997,927 B2 2/2006 Jackson
7,001,389 B1 2/2006 Navarro et al.
RE39,035 E 3/2006 Finn et al.
RE39,089 E 5/2006 Ralph et al.
7,081,116 B1 7/2006 Carly
7,087,057 B2 8/2006 Konieczynski
7,096,071 B2 8/2006 Ollivier
7,141,051 B2 11/2006 Janowski
7,179,261 B2 2/2007 Sicvol et al.
7,204,838 B2 4/2007 Jackson
7,223,268 B2 5/2007 Biedermann
7,232,104 B2 6/2007 Krapels
7,247,020 B2 7/2007 Takahashi
7,250,052 B2 7/2007 Landry et al.
7,311,563 B2 12/2007 Siebens
7,316,684 B1 1/2008 Baccelli et al.
7,320,570 B2 1/2008 Czarnek
7,334,307 B1 2/2008 Helenowski
7,490,394 B2 2/2009 Zakrzewski
7,515,220 B2 4/2009 Ko et al.
7,566,163 B2 7/2009 Inoue
7,604,655 B2 10/2009 Warnick
7,641,674 B2 1/2010 Young
7,662,172 B2 2/2010 Warnick
7,672,394 B2 3/2010 Duan et al.
7,686,833 B1 3/2010 Muhanna et al.
7,686,835 B2 3/2010 Warnick
7,717,942 B2 5/2010 Schumacher
7,717,943 B2 5/2010 Kirschman
7,766,941 B2 8/2010 Paul
7,766,943 B1 8/2010 Fallin et al.
7,766,945 B2 8/2010 Nilsson et al.
7,794,477 B2 9/2010 Melkent et al.
7,833,251 B1 11/2010 Ahlgren et al.
7,857,834 B2 12/2010 Boschert
7,862,587 B2 1/2011 Jackson
7,947,065 B2 5/2011 Hammill, Sr. et al.
7,972,364 B2 7/2011 Biedermann et al.
8,043,340 B1 10/2011 Law
8,092,494 B2 1/2012 Butler et al.
8,092,499 B1 1/2012 Roth
8,114,133 B2 2/2012 Logan
8,114,134 B2 2/2012 Winslow et al.
8,133,262 B2 3/2012 Whipple
8,162,989 B2 4/2012 Khalili
8,167,914 B1 5/2012 Hunt et al.
8,197,517 B1 6/2012 Lab et al.
8,206,422 B2 6/2012 Hestad et al.
8,211,110 B1 7/2012 Corin et al.
8,236,035 B1 8/2012 Bedor
8,377,100 B2 2/2013 Jackson
8,382,809 B2 2/2013 Kaufman et al.
8,388,659 B1 3/2013 Lab et al.
8,394,133 B2 3/2013 Jackson

(56) References Cited

U.S. PATENT DOCUMENTS 8,439,922 B1 5/2013 Arnold et al.
8,439,924 B1 5/2013 McBride et al.
8,444,681 B2 5/2013 Jackson et al.
8,470,009 B1 6/2013 Rezach
8,500,780 B2 8/2013 Petit et al.
8,801,761 B2 8/2014 Kirschman
8,814,913 B2 8/2014 Jackson
8,828,060 B2 9/2014 Biedermann et al.
8,911,479 B2 12/2014 Jackson et al.
8,998,956 B2 4/2015 George
9,068,587 B2 6/2015 Sage et al.
9,445,847 B2 9/2016 Biedermann et al.
10,004,541 B1 * 6/2018 Jackson ............ A61B 17/7032
2001/0007941 A1 7/2001 Steiner et al.
2001/0010000 A1 7/2001 Gertzbein et al.
2001/0011172 A1 8/2001 Orbay et al.
2001/0012937 A1 8/2001 Schaffler-Wachter et al.
2001/0023350 A1 9/2001 Choi
2001/0037111 A1 11/2001 Dixon et al.
2001/0041894 A1 11/2001 Campbell et al.
2001/0047173 A1 11/2001 Schlapfer et al.
2001/0047174 A1 11/2001 Donno et al.
2001/0047175 A1 11/2001 Doubler et al.
2001/0047208 A1 11/2001 Michelson
2001/0052438 A1 12/2001 Spencer
2002/0004683 A1 1/2002 Michelson
2002/0007184 A1 1/2002 Ogilvie et al.
2002/0010467 A1 1/2002 Cooper et al.
2002/0013586 A1 1/2002 Justis et al.
2002/0016594 A1 2/2002 Schlapfer et al.
2002/0022764 A1 2/2002 Smith et al.
2002/0022842 A1 2/2002 Horvath et al.
2002/0029040 A1 3/2002 Morrison et al.
2002/0035365 A1 3/2002 Kumar et al.
2002/0035366 A1 3/2002 Walder et al.
2002/0035367 A1 3/2002 Ritland
2002/0045898 A1 4/2002 Freid et al.
2002/0045899 A1 4/2002 Errico et al.
2002/0049446 A1 4/2002 Harkey, III et al.
2002/0055740 A1 5/2002 Lieberman
2002/0055741 A1 5/2002 Schlapfer et al.
2002/0058942 A1 5/2002 Biedermann et al.
2002/0068975 A1 6/2002 Teitelbaum et al.
2002/0072750 A1 6/2002 Jackson
2002/0072751 A1 6/2002 Jackson
2002/0082602 A1 6/2002 Biedermann et al.
2002/0082603 A1 6/2002 Dixon et al.
2002/0087159 A1 7/2002 Thomas
2002/0087161 A1 7/2002 Randall et al.
2002/0091386 A1 7/2002 Martin et al.
2002/0095153 A1 7/2002 Jones et al.
2002/0095154 A1 7/2002 Atkinson et al.
2002/0095881 A1 7/2002 Shreiner
2002/0103487 A1 8/2002 Errico et al.
2002/0111627 A1 8/2002 Vincent-Prestigiancomo
2002/0116001 A1 8/2002 Schaefer et al.
2002/0120270 A1 8/2002 Trieu et al.
2002/0120272 A1 8/2002 Yuan
2002/0123752 A1 9/2002 Schultheiss et al.
2002/0133154 A1 9/2002 Saint Martin
2002/0133158 A1 9/2002 Saint Martin
2002/0133159 A1 9/2002 Jackson
2002/0138076 A1 9/2002 Biedermann et al.
2002/0138077 A1 9/2002 Ferree
2002/0143328 A1 10/2002 Shluzas et al.
2002/0143330 A1 10/2002 Shluzas
2002/0143332 A1 10/2002 Lin et al.
2002/0143338 A1 10/2002 Orbay et al.
2002/0143341 A1 10/2002 Biedermann et al.
2002/0161368 A1 10/2002 Foley et al.
2002/0161370 A1 10/2002 Frigg et al.
2002/0173791 A1 11/2002 Howland
2002/0183747 A1 12/2002 Jao et al.
2002/0198526 A1 12/2002 Shaolian et al.
2003/0004519 A1 1/2003 Torode et al.
2003/0014054 A1 1/2003 Huebner
2003/0023243 A1 1/2003 Biedermann et al.
2003/0028191 A1 2/2003 Shluzas
2003/0032957 A1 2/2003 McKinley
2003/0055426 A1 3/2003 Carbone et al.
2003/0055427 A1 3/2003 Graf
2003/0060826 A1 3/2003 Foley et al.
2003/0073995 A1 4/2003 Reed
2003/0073996 A1 4/2003 Doubler et al.
2003/0073998 A1 4/2003 Pagliuca et al.
2003/0078580 A1 4/2003 Shitoto
2003/0083657 A1 5/2003 Drewry et al.
2003/0083667 A1 5/2003 Ralph et al.
2003/0088248 A1 5/2003 Reed
2003/0093077 A1 5/2003 Schlapfer et al.
2003/0093078 A1 5/2003 Ritland
2003/0100896 A1 5/2003 Biedermann et al.
2003/0100897 A1 5/2003 Metz-Stavenhagen
2003/0100904 A1 * 5/2003 Biedermann ...... A61B 17/7032 606/272
2003/0105460 A1 6/2003 Crandall et al.
2003/0109880 A1 6/2003 Shirado et al.
2003/0114852 A1 6/2003 Biedermann et al.
2003/0120275 A1 6/2003 Lenke et al.
2003/0125741 A1 7/2003 Biedermann et al.
2003/0125749 A1 7/2003 Yuan et al.
2003/0130659 A1 7/2003 Haider
2003/0130661 A1 7/2003 Osman
2003/0135210 A1 7/2003 Dixon et al.
2003/0135217 A1 7/2003 Buttermann et al.
2003/0139745 A1 7/2003 Ashman
2003/0149430 A1 8/2003 Ferrante et al.
2003/0149431 A1 8/2003 Varieur
2003/0149432 A1 8/2003 Frigg et al.
2003/0149435 A1 8/2003 Baynham et al.
2003/0153911 A1 8/2003 Shluzas
2003/0153912 A1 8/2003 Graf
2003/0153913 A1 8/2003 Altarac et al.
2003/0153920 A1 8/2003 Ralph et al.
2003/0158552 A1 8/2003 Jeon et al.
2003/0163133 A1 8/2003 Altarac et al.
2003/0167058 A1 9/2003 Shluzas
2003/0171749 A1 9/2003 Le Couedic et al.
2003/0176863 A1 9/2003 Ueyama et al.
2003/0181913 A1 9/2003 Lieberman
2003/0187433 A1 10/2003 Lin
2003/0187434 A1 10/2003 Lin
2003/0191470 A1 10/2003 Ritland
2003/0199872 A1 10/2003 Markworth et al.
2003/0199873 A1 10/2003 Richelsoph
2003/0208204 A1 11/2003 Bailey et al.
2003/0212398 A1 11/2003 Jackson
2003/0216735 A1 11/2003 Altarac et al.
2003/0220642 A1 11/2003 Freudiger
2003/0220643 A1 11/2003 Ferree
2003/0225408 A1 12/2003 Nichols et al.
2003/0229345 A1 12/2003 Stahurski
2003/0229347 A1 12/2003 Sherman et al.
2003/0236529 A1 12/2003 Shluzas et al.
2004/0006342 A1 1/2004 Altarac et al.
2004/0039383 A1 2/2004 Jackson
2004/0039384 A1 2/2004 Boehm, Jr. et al.
2004/0039385 A1 2/2004 Mazda et al.
2004/0049189 A1 3/2004 Le Couedic et al.
2004/0049190 A1 3/2004 Biedermann et al.
2004/0049196 A1 3/2004 Jackson
2004/0073215 A1 4/2004 Carli
2004/0073218 A1 4/2004 Dahners
2004/0078051 A1 4/2004 Davison et al.
2004/0078082 A1 4/2004 Lange
2004/0143265 A1 4/2004 Landry et al.
2004/0220671 A1 4/2004 Ralph et al.
2004/0087949 A1 5/2004 Bono et al.
2004/0087950 A1 5/2004 Teitelbaum
2004/0087952 A1 5/2004 Borgstrom et al.
2004/0092934 A1 5/2004 Howland
2004/0092938 A1 5/2004 Carli
2004/0097933 A1 5/2004 Lourdel et al.
2004/0106925 A1 6/2004 Culbert

(56) References Cited

U.S. PATENT DOCUMENTS

2004/0111091 A1 6/2004 Ogilvie et al.
2004/0122442 A1 6/2004 Lewis
2004/0127897 A1 7/2004 Freid et al.
2004/0127904 A1 7/2004 Konieczynski et al.
2004/0133207 A1 7/2004 Abdou
2004/0138660 A1 7/2004 Serhan
2004/0138662 A1 7/2004 Landry et al.
2004/0147928 A1 7/2004 Landry et al.
2004/0147929 A1 7/2004 Biedermann et al.
2004/0147937 A1 7/2004 Dunbar, Jr. et al.
2004/0153068 A1* 8/2004 Janowski ........... A61B 17/7037 606/272
2004/0158245 A1 8/2004 Chin
2004/0158247 A1 8/2004 Sitiso et al.
2004/0158258 A1 8/2004 Bonati et al.
2004/0162560 A1 8/2004 Raynor et al.
2004/0167523 A1 8/2004 Jackson
2004/0167524 A1 8/2004 Jackson
2004/0167525 A1 8/2004 Jackson
2004/0172025 A1 9/2004 Drewry et al.
2004/0172031 A1 9/2004 Rubecamp et al.
2004/0172032 A1 9/2004 Jackson
2004/0176766 A1 9/2004 Shluzas
2004/0176776 A1 9/2004 Zubok et al.
2004/0186473 A1 9/2004 Cournoyer et al.
2004/0186474 A1 9/2004 Matthis et al.
2004/0186475 A1 9/2004 Falahee
2004/0210216 A1 10/2004 Farris et al.
2004/0210227 A1 10/2004 Trail et al.
2004/0215190 A1 10/2004 Nguyen et al.
2004/0215191 A1 10/2004 Kitchen
2004/0220567 A1 11/2004 Eisermann et al.
2004/0225289 A1 11/2004 Biedermann et al.
2004/0230100 A1 11/2004 Shluzas
2004/0236327 A1 11/2004 Paul et al.
2004/0236328 A1 11/2004 Paul et al.
2004/0236330 A1 11/2004 Purcell et al.
2004/0249378 A1 12/2004 Saint Martin et al.
2004/0254574 A1 12/2004 Morrison et al.
2004/0260283 A1 12/2004 Wu et al.
2004/0267264 A1 12/2004 Konieczynski et al.
2005/0010219 A1 1/2005 Dalton
2005/0010220 A1 1/2005 Casutt et al.
2005/0021036 A1 1/2005 Whitemore et al.
2005/0027296 A1 2/2005 Thramann et al.
2005/0033298 A1 2/2005 Hawkes et al.
2005/0033436 A1 2/2005 Schlapfer et al.
2005/0033439 A1 2/2005 Gordon et al.
2005/0038430 A1 2/2005 McKinley
2005/0038432 A1 2/2005 Shaolian et al.
2005/0038433 A1 2/2005 Young
2005/0049588 A1 3/2005 Jackson
2005/0049589 A1 3/2005 Jackson
2005/0055026 A1 3/2005 Biedermann et al.
2005/0065514 A1 3/2005 Studer
2005/0065515 A1 3/2005 Jahng
2005/0065516 A1 3/2005 Jahng
2005/0065517 A1 3/2005 Chin
2005/0070899 A1 3/2005 Doubler et al.
2005/0070901 A1 3/2005 David
2005/0080415 A1 4/2005 Keyer et al.
2005/0085812 A1 4/2005 Sherman et al.
2005/0085813 A1 4/2005 Spitler et al.
2005/0085815 A1 4/2005 Harms et al.
2005/0085816 A1 4/2005 Michelson
2005/0090821 A1 4/2005 Berrevoets et al.
2005/0096652 A1 5/2005 Burton
2005/0096653 A1 5/2005 Doubler et al.
2005/0096654 A1 5/2005 Lin
2005/0107788 A1 5/2005 Beaurain et al.
2005/0113927 A1 5/2005 Malek
2005/0119658 A1 6/2005 Ralph et al.
2005/0124991 A1 6/2005 Jahng
2005/0131404 A1 6/2005 Mazda et al.
2005/0131405 A1 6/2005 Molz, IV et al.
2005/0131406 A1 6/2005 Reiley et al.
2005/0131407 A1 6/2005 Sicvol et al.
2005/0131408 A1 6/2005 Sicvol et al.
2005/0131413 A1 6/2005 O'Driscoll et al.
2005/0131419 A1 6/2005 McCord et al.
2005/0131421 A1 6/2005 Anderson et al.
2005/0131422 A1 6/2005 Anderson
2005/0137594 A1 6/2005 Doubler et al.
2005/0137597 A1 6/2005 Butler et al.
2005/0141986 A1 6/2005 Flesher
2005/0143737 A1 6/2005 Pafford et al.
2005/0143823 A1 6/2005 Boyd et al.
2005/0144389 A1 7/2005 Selover et al.
2005/0149020 A1 7/2005 Jahng
2005/0149053 A1 7/2005 Varieur
2005/0154390 A1 7/2005 Biedermann et al.
2005/0154391 A1 7/2005 Doherty et al.
2005/0159750 A1 7/2005 Doherty
2005/0165400 A1 7/2005 Fernandez
2005/0171540 A1 8/2005 Lim et al.
2005/0171543 A1 8/2005 Timm et al.
2005/0177154 A1 8/2005 Moumene et al.
2005/0177166 A1 8/2005 Timm et al.
2005/0182401 A1 8/2005 Timm et al.
2005/0182410 A1 8/2005 Jackson
2005/0187548 A1 8/2005 Butler et al.
2005/0187555 A1 8/2005 Biedermann et al.
2005/0192571 A1 9/2005 Abdelgany
2005/0192572 A1 9/2005 Abdelgany et al.
2005/0192573 A1 9/2005 Abdelgany et al.
2005/0192579 A1 9/2005 Jackson
2005/0192580 A1 9/2005 Dalton
2005/0192589 A1 9/2005 Raymond et al.
2005/0203511 A1 9/2005 Wilson-MacDonald et al.
2005/0203513 A1 9/2005 Jahng et al.
2005/0203514 A1 9/2005 Jahng et al.
2005/0203516 A1 9/2005 Harms et al.
2005/0203518 A1 9/2005 Biederman et al.
2005/0203519 A1 9/2005 Harms et al.
2005/0215999 A1 9/2005 Birkmeyer et al.
2005/0216000 A1 9/2005 Colleran et al.
2005/0216001 A1 9/2005 David
2005/0216003 A1 9/2005 Biedermann et al.
2005/0228326 A1 10/2005 Kalfas et al.
2005/0228379 A1 10/2005 Jackson
2005/0228385 A1 10/2005 Lee et al.
2005/0228400 A1 10/2005 Chao
2005/0228501 A1 10/2005 Miller et al.
2005/0234450 A1 10/2005 Barker
2005/0234451 A1 10/2005 Markworth
2005/0234452 A1 10/2005 Malandain
2005/0234453 A1 10/2005 Shaolian et al.
2005/0234454 A1 10/2005 Chin
2005/0234456 A1 10/2005 Malandain
2005/0234459 A1 10/2005 Falahee et al.
2005/0240181 A1 10/2005 Boomer et al.
2005/0240183 A1 10/2005 Vaughan
2005/0245930 A1 11/2005 Timm et al.
2005/0251137 A1 11/2005 Ball
2005/0251139 A1 11/2005 Roh
2005/0251140 A1 11/2005 Shaolian et al.
2005/0251141 A1 11/2005 Frigg et al.
2005/0260058 A1 11/2005 Casagne, III
2005/0261687 A1 11/2005 Garamszegi et al.
2005/0267470 A1 12/2005 McBride
2005/0267471 A1 12/2005 Biedermann et al.
2005/0267472 A1 12/2005 Biedermann et al.
2005/0267474 A1 12/2005 Dalton
2005/0267477 A1 12/2005 Jackson
2005/0273099 A1 12/2005 Baccelli et al.
2005/0273101 A1 12/2005 Schumacher
2005/0277919 A1 12/2005 Slivka et al.
2005/0277922 A1 12/2005 Trieu et al.
2005/0277923 A1 12/2005 Sweeney
2005/0277925 A1 12/2005 Mujwid
2005/0277927 A1 12/2005 Guenther et al.
2005/0277928 A1 12/2005 Boschert
2005/0277931 A1 12/2005 Sweeney et al.
2005/0277934 A1 12/2005 Vardiman

(56) References Cited

U.S. PATENT DOCUMENTS

2005/0278023 A1 12/2005 Zwirkoski
2005/0283152 A1 12/2005 Lindemann et al.
2005/0283157 A1 12/2005 Coates et al.
2005/0283238 A1 12/2005 Reiley
2005/0283244 A1 12/2005 Gordon et al.
2005/0288669 A1 12/2005 Abdou
2005/0288670 A1 12/2005 Panjabi
2005/0288672 A1 12/2005 Ferree
2005/0288673 A1 12/2005 Catbagan et al.
2006/0004359 A1 1/2006 Kramer et al.
2006/0004363 A1 1/2006 Brookmeyer et al.
2006/0009767 A1 1/2006 Kiester
2006/0009769 A1 1/2006 Lieberman
2006/0009770 A1 1/2006 Speirs et al.
2006/0009773 A1 1/2006 Jackson
2006/0009780 A1 1/2006 Foley et al.
2006/0015099 A1 1/2006 Cannon et al.
2006/0025767 A1 2/2006 Khalili
2006/0025768 A1 2/2006 Iott et al.
2006/0025770 A1 2/2006 Schlapfer et al.
2006/0025771 A1 2/2006 Jackson
2006/0030850 A1 2/2006 Keegan et al.
2006/0036240 A1 2/2006 Colleran et al.
2006/0036242 A1 2/2006 Nilsson et al.
2006/0036243 A1 2/2006 Sasso et al.
2006/0036244 A1 2/2006 Spitler et al.
2006/0036246 A1 2/2006 Carl et al.
2006/0036252 A1 2/2006 Baynham et al.
2006/0036254 A1 2/2006 Lim
2006/0036256 A1 2/2006 Carl et al.
2006/0036259 A1 2/2006 Carl et al.
2006/0036323 A1 2/2006 Carl et al.
2006/0036324 A1 2/2006 Sachs et al.
2006/0052780 A1 3/2006 Errico et al.
2006/0052783 A1 3/2006 Dant et al.
2006/0052784 A1 3/2006 Dant et al.
2006/0052786 A1 3/2006 Dant et al.
2006/0058788 A1 3/2006 Hammer et al.
2006/0058790 A1 3/2006 Carl et al.
2006/0064090 A1 3/2006 Park
2006/0064091 A1 3/2006 Ludwig et al.
2006/0064092 A1 3/2006 Howland
2006/0069390 A1 3/2006 Frigg et al.
2006/0074418 A1 4/2006 Jackson
2006/0074419 A1 4/2006 Taylor et al.
2006/0079893 A1 4/2006 Jackson
2006/0079894 A1 4/2006 Colleran et al.
2006/0079895 A1 4/2006 McLeer
2006/0079896 A1 4/2006 Kwak et al.
2006/0079898 A1 4/2006 Ainsworth
2006/0079899 A1 4/2006 Ritland
2006/0083603 A1 4/2006 Jackson
2006/0084977 A1 4/2006 Liberman
2006/0084980 A1 4/2006 Melkent et al.
2006/0084981 A1 4/2006 Shluzas
2006/0084982 A1 4/2006 Dickinson et al.
2006/0084983 A1 4/2006 Kim
2006/0084984 A1 4/2006 Kim
2006/0084985 A1 4/2006 Kim
2006/0084987 A1 4/2006 Kim
2006/0084988 A1 4/2006 Kim
2006/0084991 A1 4/2006 Borgstrom et al.
2006/0085069 A1 4/2006 Kim
2006/0085070 A1 4/2006 Kim
2006/0089643 A1 4/2006 Mujwid
2006/0089644 A1 4/2006 Felix
2006/0089645 A1 4/2006 Eckman
2006/0095035 A1 5/2006 Jones et al.
2006/0095037 A1 5/2006 Jones et al.
2006/0095038 A1 5/2006 Jackson
2006/0100621 A1 5/2006 Jackson
2006/0100622 A1 5/2006 Jackson
2006/0106381 A1 5/2006 Ferree et al.
2006/0106394 A1 5/2006 Colleran
2006/0111713 A1 5/2006 Jackson
2006/0111715 A1 5/2006 Jackson
2006/0116677 A1 6/2006 Burd et al.
2006/0122597 A1 6/2006 Jones et al.
2006/0122599 A1 6/2006 Drewry et al.
2006/0129147 A1 6/2006 Biedermann et al.
2006/0129149 A1 6/2006 Iott et al.
2006/0129239 A1 6/2006 Kwak
2006/0131421 A1 6/2006 Dunn et al.
2006/0142758 A1 6/2006 Petit
2006/0142760 A1 6/2006 McDonnell
2006/0149228 A1 7/2006 Schlapfer et al.
2006/0149229 A1 7/2006 Kwak et al.
2006/0149232 A1 7/2006 Sasing
2006/0149235 A1 7/2006 Jackson
2006/0149238 A1 7/2006 Sherman et al.
2006/0149240 A1 7/2006 Jackson
2006/0149241 A1 7/2006 Richelsoph et al.
2006/0149251 A1 7/2006 Ziolo et al.
2006/0155277 A1 7/2006 Metz-Stavenhagen
2006/0155278 A1 7/2006 Warnick
2006/0161152 A1 7/2006 Ensign et al.
2006/0166535 A1 7/2006 Brumfield et al.
2006/0167454 A1 7/2006 Ludwig et al.
2006/0167455 A1 7/2006 Clement et al.
2006/0173454 A1 8/2006 Spitler et al.
2006/0173456 A1 8/2006 Hawkes et al.
2006/0184171 A1 8/2006 Biedermann et al.
2006/0184180 A1 8/2006 Augostino et al.
2006/0189983 A1 8/2006 Fallin et al.
2006/0189985 A1 8/2006 Lewis
2006/0195090 A1 8/2006 Suddaby
2006/0195093 A1 8/2006 Jahng
2006/0195198 A1 8/2006 James
2006/0200023 A1 9/2006 Melkent et al.
2006/0200128 A1 9/2006 Mueller
2006/0200130 A1 9/2006 Hawkins et al.
2006/0200131 A1 9/2006 Chao et al.
2006/0200132 A1 9/2006 Chao et al.
2006/0200133 A1 9/2006 Jackson
2006/0200149 A1 9/2006 Hoy et al.
2006/0212033 A1 9/2006 Rothman et al.
2006/0212034 A1 9/2006 Triplett et al.
2006/0217713 A1 9/2006 Serhan et al.
2006/0217716 A1 9/2006 Baker et al.
2006/0217719 A1 9/2006 Albert et al.
2006/0229608 A1 10/2006 Foster et al.
2006/0229609 A1 10/2006 Wang
2006/0229613 A1 10/2006 Timm
2006/0229614 A1 10/2006 Foley et al.
2006/0229615 A1 10/2006 Abdou
2006/0241593 A1 10/2006 Sherman et al.
2006/0241595 A1 10/2006 Molz, IV et al.
2006/0241600 A1 10/2006 Ensign et al.
2006/0241601 A1 10/2006 Trautwein et al.
2006/0241603 A1 10/2006 Jackson
2006/0247624 A1 11/2006 Banouskou et al.
2006/0247630 A1 11/2006 Iott et al.
2006/0247631 A1 11/2006 Ahn et al.
2006/0247632 A1 11/2006 Winslow et al.
2006/0247633 A1 11/2006 Winslow et al.
2006/0247635 A1 11/2006 Gordon et al.
2006/0247658 A1 11/2006 Pond, Jr. et al.
2006/0247779 A1 11/2006 Gordon
2006/0260483 A1 11/2006 Hartmann et al.
2006/0264933 A1 11/2006 Baker et al.
2006/0264934 A1 11/2006 Fallin
2006/0264935 A1 11/2006 White
2006/0264936 A1 11/2006 Partin et al.
2006/0264962 A1 11/2006 Chin et al.
2006/0276787 A1 12/2006 Zubok et al.
2006/0276789 A1 12/2006 Jackson
2006/0276791 A1 12/2006 Shluzas
2006/0276792 A1 12/2006 Ensign et al.
2006/0282075 A1 12/2006 Labrom et al.
2006/0282076 A1 12/2006 Labrom et al.
2006/0282077 A1 12/2006 Labrom et al.
2006/0282078 A1 12/2006 Labrom et al.
2006/0282079 A1 12/2006 Labrom et al.
2006/0282080 A1 12/2006 Albert

(56) References Cited

U.S. PATENT DOCUMENTS

2006/0293657 A1 12/2006 Hartmann
2006/0293659 A1 12/2006 Alvarez
2006/0293663 A1 12/2006 Walkenhorst
2006/0293666 A1 12/2006 Matthis et al.
2006/0293693 A1 12/2006 Farr et al.
2007/0005062 A1 1/2007 Lange et al.
2007/0005063 A1 1/2007 Bruneau et al.
2007/0005137 A1 1/2007 Kwak
2007/0016190 A1 1/2007 Martinez et al.
2007/0016194 A1 1/2007 Shaolian et al.
2007/0016200 A1 1/2007 Jackson
2007/0021750 A1 1/2007 Shluzas et al.
2007/0032123 A1 2/2007 Timm et al.
2007/0043356 A1 2/2007 Timm et al.
2007/0043357 A1 2/2007 Kirschman
2007/0043358 A1 2/2007 Molz, IV et al.
2007/0043359 A1 2/2007 Altarac et al.
2007/0043364 A1 2/2007 Cawley et al.
2007/0049931 A1 3/2007 Justis et al.
2007/0049933 A1 3/2007 Ahn et al.
2007/0049936 A1 3/2007 Colleran et al.
2007/0055236 A1 3/2007 Hudgins et al.
2007/0055239 A1 3/2007 Sweeney et al.
2007/0055240 A1 3/2007 Matthis et al.
2007/0055241 A1 3/2007 Matthis et al.
2007/0055242 A1 3/2007 Bailly
2007/0055244 A1 3/2007 Jackson
2007/0073289 A1 3/2007 Kwak et al.
2007/0073290 A1 3/2007 Boehm, Jr.
2007/0073291 A1 3/2007 Cordaro et al.
2007/0073293 A1 3/2007 Martz et al.
2007/0073294 A1 3/2007 Chin et al.
2007/0078460 A1 4/2007 Frigg et al.
2007/0078461 A1 4/2007 Shluzas
2007/0083199 A1 4/2007 Baccelli
2007/0088357 A1 4/2007 Johnson et al.
2007/0088359 A1 4/2007 Woods et al.
2007/0090238 A1 4/2007 Justis
2007/0093813 A1 4/2007 Callahan et al.
2007/0093814 A1 4/2007 Callahan, II et al.
2007/0093815 A1 4/2007 Callahan, II et al.
2007/0093818 A1 4/2007 Biedermann et al.
2007/0093819 A1 4/2007 Albert
2007/0093824 A1 4/2007 Hestad et al.
2007/0093826 A1 4/2007 Hawkes et al.
2007/0093827 A1 4/2007 Warnick
2007/0093833 A1 4/2007 Kuiper et al.
2007/0100341 A1 5/2007 Reglos et al.
2007/0118117 A1 5/2007 Altarac et al.
2007/0118118 A1 5/2007 Kwak et al.
2007/0118119 A1 5/2007 Hestad
2007/0118122 A1 5/2007 Butler et al.
2007/0118123 A1 5/2007 Strausbaugh et al.
2007/0118124 A1 5/2007 Biedermann et al.
2007/0123862 A1 5/2007 Warnick
2007/0123867 A1 5/2007 Kirschman
2007/0123870 A1 5/2007 Jeon et al.
2007/0129729 A1 6/2007 Petit et al.
2007/0156142 A1 7/2007 Rezach et al.
2007/0161986 A1 7/2007 Levy
2007/0161991 A1 7/2007 Altarac et al.
2007/0161994 A1 7/2007 Lowrey et al.
2007/0161995 A1 7/2007 Trautwein et al.
2007/0161996 A1 7/2007 Biedermann et al.
2007/0161997 A1 7/2007 Thramann et al.
2007/0161999 A1 7/2007 Biedermann et al.
2007/0167948 A1 7/2007 Abdou
2007/0167949 A1 7/2007 Altarac et al.
2007/0173818 A1 7/2007 Hestad et al.
2007/0173819 A1 7/2007 Sandlin
2007/0173820 A1 7/2007 Trieu
2007/0173822 A1 7/2007 Bruneau et al.
2007/0173828 A1 7/2007 Firkins et al.
2007/0173832 A1 7/2007 Tebbe et al.
2007/0191832 A1 8/2007 Trieu
2007/0191839 A1 8/2007 Justis et al.
2007/0191841 A1 8/2007 Justis et al.
2007/0191846 A1 8/2007 Bruneau et al.
2007/0198014 A1 8/2007 Graf et al.
2007/0208344 A1 9/2007 Young
2007/0213720 A1 9/2007 Gordon et al.
2007/0219554 A1 9/2007 Landry et al.
2007/0225707 A1 9/2007 Wisnewski et al.
2007/0225708 A1 9/2007 Biedermann et al.
2007/0225711 A1 9/2007 Ensign
2007/0233073 A1 10/2007 Wisnewski et al.
2007/0233078 A1 10/2007 Justis et al.
2007/0233080 A1 10/2007 Na et al.
2007/0233085 A1 10/2007 Biedermann et al.
2007/0233086 A1 10/2007 Harms et al.
2007/0233089 A1 10/2007 Dipoto et al.
2007/0233092 A1 10/2007 Falahee
2007/0233094 A1 10/2007 Colleran et al.
2007/0233095 A1 10/2007 Schlapfer
2007/0233155 A1 10/2007 Lovell
2007/0244481 A1 10/2007 Timm
2007/0244482 A1 10/2007 Aferzon
2007/0250061 A1 10/2007 Chin et al.
2007/0260243 A1 11/2007 Kagami
2007/0260246 A1 11/2007 Biedermann
2007/0270813 A1 11/2007 Garamszegi
2007/0270821 A1 11/2007 Trieu et al.
2007/0270832 A1 11/2007 Moore
2007/0270836 A1 11/2007 Bruneau et al.
2007/0270837 A1 11/2007 Eckhardt et al.
2007/0270838 A1 11/2007 Bruneau et al.
2007/0270843 A1 11/2007 Matthis et al.
2007/0270869 A1 11/2007 Young et al.
2007/0276371 A1 11/2007 Baynham et al.
2007/0276379 A1 11/2007 Miller et al.
2007/0276380 A1 11/2007 Jahng et al.
2007/0288004 A1 12/2007 Alvarez
2007/0288012 A1 12/2007 Colleran et al.
2007/0293862 A1 12/2007 Jackson
2008/0009862 A1 1/2008 Hoffman
2008/0009864 A1 1/2008 Forton et al.
2008/0015578 A1 1/2008 Erickson et al.
2008/0015579 A1 1/2008 Whipple
2008/0015580 A1 1/2008 Chao
2008/0015596 A1 1/2008 Whipple
2008/0015597 A1 1/2008 Whipple
2008/0021454 A1 1/2008 Chao et al.
2008/0021455 A1 1/2008 Chao et al.
2008/0021462 A1 1/2008 Trieu
2008/0021464 A1 1/2008 Morin et al.
2008/0021465 A1 1/2008 Shadduck et al.
2008/0027432 A1 1/2008 Strauss et al.
2008/0039843 A1 2/2008 Abdou
2008/0039848 A1 2/2008 Jackson
2008/0045951 A1 2/2008 Fanger et al.
2008/0045953 A1 2/2008 Garamszegi
2008/0045955 A1 2/2008 Berrevoets et al.
2008/0051780 A1 2/2008 Vaidya et al.
2008/0051787 A1 2/2008 Remington et al.
2008/0058811 A1 3/2008 Alleyne et al.
2008/0058812 A1 3/2008 Zehnder
2008/0065071 A1 3/2008 Park
2008/0065073 A1 3/2008 Perriello et al.
2008/0065075 A1 3/2008 Dant
2008/0065077 A1 3/2008 Ferree
2008/0065079 A1 3/2008 Bruneau et al.
2008/0071273 A1 3/2008 Hawkes et al.
2008/0071274 A1 3/2008 Ensign
2008/0071277 A1 3/2008 Warnick
2008/0077136 A1 3/2008 Triplett et al.
2008/0077138 A1 3/2008 Cohen et al.
2008/0077139 A1 3/2008 Landry et al.
2008/0077143 A1 3/2008 Shluzas
2008/0086131 A1 4/2008 Daly et al.
2008/0086132 A1 4/2008 Biedermann et al.
2008/0091213 A1 4/2008 Jackson
2008/0097441 A1 4/2008 Hayes et al.
2008/0097457 A1 4/2008 Warnick
2008/0103502 A1 5/2008 Capote et al.

(56) References Cited

U.S. PATENT DOCUMENTS

2008/0108992 A1 5/2008 Barry et al.
2008/0114362 A1 5/2008 Justis et al.
2008/0114403 A1 5/2008 Kuester et al.
2008/0119849 A1 5/2008 Beardsley et al.
2008/0119857 A1 5/2008 Potash et al.
2008/0119858 A1 5/2008 Potash
2008/0125777 A1 5/2008 Veldman et al.
2008/0125787 A1 5/2008 Doubler et al.
2008/0125813 A1 5/2008 Erickson et al.
2008/0132957 A1 6/2008 Matthis et al.
2008/0140075 A1 6/2008 Ensign et al.
2008/0140076 A1 6/2008 Jackson
2008/0140133 A1 6/2008 Allard et al.
2008/0140136 A1 6/2008 Jackson
2008/0147121 A1 6/2008 Justis et al.
2008/0147122 A1 6/2008 Jackson
2008/0147129 A1 6/2008 Biedermann et al.
2008/0147195 A1 6/2008 Kwak et al.
2008/0154279 A1 6/2008 Schumaker et al.
2008/0154308 A1 6/2008 Sherman et al.
2008/0154315 A1 6/2008 Jackson
2008/0161857 A1 7/2008 Hestad et al.
2008/0161863 A1 7/2008 Arnold et al.
2008/0167687 A1 7/2008 Colleran et al.
2008/0167689 A1 7/2008 Matthis et al.
2008/0172090 A1 7/2008 Molz
2008/0172091 A1 7/2008 Anderson
2008/0172096 A1 7/2008 Hawkins
2008/0177316 A1 7/2008 Bergeron et al.
2008/0177317 A1 7/2008 Jackson
2008/0177321 A1 7/2008 Drewry et al.
2008/0177322 A1 7/2008 Davis et al.
2008/0177323 A1 7/2008 Null et al.
2008/0177388 A1 7/2008 Patterson et al.
2008/0183212 A1 7/2008 Veldman et al.
2008/0183213 A1 7/2008 Veldman et al.
2008/0183215 A1 7/2008 Altarac et al.
2008/0183216 A1 7/2008 Jackson
2008/0183219 A1 7/2008 Jackson
2008/0183223 A1 7/2008 Jeon et al.
2008/0188898 A1 8/2008 Jackson
2008/0195153 A1 8/2008 Thompson
2008/0195155 A1 8/2008 Hoffman et al.
2008/0195159 A1 8/2008 Kloss et al.
2008/0200918 A1 8/2008 Spitler et al.
2008/0200956 A1 8/2008 Beckwith et al.
2008/0215095 A1 9/2008 Biedermann et al.
2008/0215100 A1 9/2008 Matthis et al.
2008/0228184 A1 9/2008 Hestad
2008/0228228 A1 9/2008 Hestad et al.
2008/0234736 A1 9/2008 Trieu et al.
2008/0234737 A1 9/2008 Boschert
2008/0234738 A1 9/2008 Zylber et al.
2008/0234739 A1 9/2008 Hudgins et al.
2008/0234744 A1 9/2008 Zylber et al.
2008/0234756 A1 9/2008 Sutcliffe et al.
2008/0234759 A1 9/2008 Marino
2008/0234761 A1 9/2008 Jackson
2008/0243052 A1 10/2008 Pond et al.
2008/0243185 A1 10/2008 Felix et al.
2008/0243193 A1 10/2008 Ensign et al.
2008/0249570 A1 10/2008 Carson et al.
2008/0249576 A1 10/2008 Hawkes et al.
2008/0262548 A1 10/2008 Lange et al.
2008/0262551 A1 10/2008 Rice et al.
2008/0262554 A1 10/2008 Hayes et al.
2008/0262556 A1 10/2008 Jacofsky et al.
2008/0269742 A1 10/2008 Levy et al.
2008/0269804 A1 10/2008 Holt
2008/0269805 A1 10/2008 Dekutoski et al.
2008/0269809 A1 10/2008 Garamszegi
2008/0275456 A1 11/2008 Vonwiller et al.
2008/0275504 A1 11/2008 Bonin et al.
2008/0287994 A1 11/2008 Perez-Cruet et al.
2008/0288002 A1 11/2008 Crall et al.
2008/0292429 A1 11/2008 Hasenbohler et al.
2008/0294203 A1 11/2008 Kovach et al.
2008/0300630 A1 12/2008 Bonnema et al.
2008/0300631 A1 12/2008 Tornier
2008/0300633 A1 12/2008 Jackson
2008/0306513 A1 12/2008 Winslow et al.
2008/0306525 A1 12/2008 Winslow et al.
2008/0306526 A1 12/2008 Winslow et al.
2008/0306533 A1 12/2008 Winslow et al.
2008/0306536 A1 12/2008 Frigg et al.
2008/0306540 A1 12/2008 Mitchell et al.
2008/0306543 A1 12/2008 Cain et al.
2008/0312655 A1 12/2008 Kirschman et al.
2008/0312692 A1 12/2008 Brennan et al.
2008/0312696 A1 12/2008 Butters et al.
2008/0312701 A1 12/2008 Butters et al.
2008/0312703 A1 12/2008 Hestad et al.
2008/0312704 A1 12/2008 Hestad et al.
2008/0319482 A1 12/2008 Jackson
2008/0319490 A1 12/2008 Jackson
2009/0005787 A1 1/2009 Crall et al.
2009/0005813 A1 1/2009 Crall et al.
2009/0005814 A1 1/2009 Miller et al.
2009/0012562 A1 1/2009 Hestad et al.
2009/0012567 A1 1/2009 Biedermann et al.
2009/0018557 A1 1/2009 Pisharodi
2009/0018583 A1 1/2009 Song et al.
2009/0024165 A1 1/2009 Ferree
2009/0024169 A1 1/2009 Triplett et al.
2009/0030457 A1 1/2009 Janowski et al.
2009/0030464 A1 1/2009 Hestad et al.
2009/0036929 A1 2/2009 Reglos et al.
2009/0036932 A1 2/2009 Rouyer et al.
2009/0036934 A1 2/2009 Biedermann et al.
2009/0048601 A1 2/2009 Forton et al.
2009/0048631 A1 2/2009 Bhatnagar et al.
2009/0062860 A1 3/2009 Fraiser et al.
2009/0062865 A1 3/2009 Schumacher
2009/0062866 A1 3/2009 Jackson
2009/0062867 A1 3/2009 Schumacher
2009/0062914 A1 3/2009 Marino
2009/0069849 A1 3/2009 Oh et al.
2009/0069852 A1 3/2009 Farris et al.
2009/0069853 A1 3/2009 Schumacher
2009/0076550 A1 3/2009 Bernhardt, Jr. et al.
2009/0076552 A1 3/2009 Tornier
2009/0082666 A1 3/2009 Geist et al.
2009/0082812 A1 3/2009 Lewis
2009/0082815 A1 3/2009 Zylber et al.
2009/0082819 A1 3/2009 Blain et al.
2009/0088769 A1 4/2009 Poletti
2009/0088799 A1 4/2009 Yeh
2009/0088803 A1 4/2009 Justis et al.
2009/0088807 A1 4/2009 Castaneda et al.
2009/0093820 A1 4/2009 Trieu et al.
2009/0093843 A1 4/2009 Lemoine et al.
2009/0093844 A1 4/2009 Jackson
2009/0093846 A1 4/2009 Hestad et al.
2009/0099606 A1 4/2009 Hestad et al.
2009/0099608 A1 4/2009 Szczesny
2009/0105769 A1 4/2009 Rock et al.
2009/0105770 A1 4/2009 Berrevoets et al.
2009/0105771 A1 4/2009 Lei et al.
2009/0105820 A1 4/2009 Jackson
2009/0112265 A1 4/2009 Hudgins et al.
2009/0112266 A1 4/2009 Weng et al.
2009/0112269 A1 4/2009 Lieberman et al.
2009/0118772 A1 5/2009 Diederich et al.
2009/0131983 A1 5/2009 Biedermann et al.
2009/0138044 A1 5/2009 Bergeron et al.
2009/0138052 A1 5/2009 Biedermann et al.
2009/0143827 A1 6/2009 Levy et al.
2009/0143828 A1 6/2009 Stad et al.
2009/0149885 A1 6/2009 Durward et al.
2009/0149892 A1 6/2009 Stad et al.
2009/0157120 A1 6/2009 Marino et al.
2009/0163901 A1 6/2009 Fisher et al.
2009/0163953 A1 6/2009 Biedermann et al.
2009/0163954 A1 6/2009 Kwak

(56) References Cited

U.S. PATENT DOCUMENTS

2009/0163955 A1 6/2009 Moumene et al.
2009/0163956 A1 6/2009 Biedermann et al.
2009/0163961 A1 6/2009 Kirschman
2009/0163963 A1 6/2009 Berrevoets
2009/0171392 A1 7/2009 Garcia-Bengochea et al.
2009/0171395 A1 7/2009 Jeon et al.
2009/0177232 A1 7/2009 Kiester
2009/0177237 A1 7/2009 Zucherman et al.
2009/0182380 A1 7/2009 Abdelgany
2009/0182430 A1 7/2009 Tyber et al.
2009/0192548 A1 7/2009 Jeon et al.
2009/0192551 A1 7/2009 Cianfrani et al.
2009/0198280 A1 8/2009 Spratt et al.
2009/0198281 A1 8/2009 Rice et al.
2009/0198289 A1 8/2009 Manderson
2009/0198291 A1 8/2009 Kevin et al.
2009/0204155 A1 8/2009 Aschmann
2009/0216278 A1 8/2009 Song
2009/0216280 A1 8/2009 Hutchinson
2009/0221877 A1 9/2009 Woods
2009/0221879 A1 9/2009 Gorek
2009/0228045 A1 9/2009 Hayes et al.
2009/0240292 A1 9/2009 Butler et al.
2009/0248030 A1 10/2009 Butler et al.
2009/0248075 A1 10/2009 Ogilvie et al.
2009/0248077 A1 10/2009 Johns
2009/0248083 A1 10/2009 Patterson et al.
2009/0248088 A1 10/2009 Biedermann
2009/0254125 A1 10/2009 Predick
2009/0259254 A1 10/2009 Pisharodi
2009/0259257 A1 10/2009 Prevost
2009/0259258 A1 10/2009 Perez-Cruet et al.
2009/0264895 A1 10/2009 Gasperut et al.
2009/0264896 A1 10/2009 Biedermann et al.
2009/0264930 A1 10/2009 McBride
2009/0264933 A1 10/2009 Carls et al.
2009/0270916 A1 10/2009 Ramsay et al.
2009/0270917 A1 10/2009 Boehm
2009/0270920 A1 10/2009 Douget et al.
2009/0270921 A1 10/2009 Krause
2009/0270922 A1 10/2009 Biedermann et al.
2009/0275981 A1 11/2009 Abdelgany et al.
2009/0275983 A1 11/2009 Veldman et al.
2009/0275985 A1 11/2009 Jackson
2009/0275986 A1 11/2009 Prevost et al.
2009/0281542 A1 11/2009 Justis
2009/0281571 A1 11/2009 Weaver et al.
2009/0281572 A1 11/2009 White
2009/0281573 A1 11/2009 Biedermann et al.
2009/0281574 A1 11/2009 Jackson
2009/0287252 A1 11/2009 Marik et al.
2009/0287253 A1 11/2009 Felix et al.
2009/0299411 A1 12/2009 Laskowitz et al.
2009/0299415 A1 12/2009 Pimenta
2009/0306719 A1 12/2009 Meyer, III et al.
2009/0306720 A1 12/2009 Doubler et al.
2009/0312804 A1 12/2009 Gamache et al.
2009/0326582 A1 12/2009 Songer et al.
2009/0326583 A1 12/2009 Moumene et al.
2009/0326586 A1 12/2009 Duarte
2010/0004692 A1 1/2010 Biedermann et al.
2010/0004694 A1 1/2010 Little
2010/0004695 A1 1/2010 Stad et al.
2010/0010540 A1 1/2010 Park
2010/0010542 A1 1/2010 Jackson
2010/0010543 A1 1/2010 Jackson
2010/0023061 A1 1/2010 Randol et al.
2010/0030224 A1 2/2010 Winslow et al.
2010/0030272 A1 2/2010 Winslow et al.
2010/0030283 A1 2/2010 King et al.
2010/0036417 A1 2/2010 James et al.
2010/0036422 A1 2/2010 Flynn et al.
2010/0036423 A1 2/2010 Hayes et al.
2010/0036425 A1 2/2010 Barrus et al.
2010/0036432 A1 2/2010 Ely
2010/0036443 A1 2/2010 Hutton et al.
2010/0042149 A1 2/2010 Chao et al.
2010/0042152 A1 2/2010 Semler et al.
2010/0042155 A1 2/2010 Biedermann et al.
2010/0042156 A1 2/2010 Harms et al.
2010/0057125 A1 3/2010 Viker
2010/0057126 A1 3/2010 Hestad
2010/0057131 A1 3/2010 Ely
2010/0063544 A1 3/2010 Butler
2010/0063545 A1 3/2010 Richelsoph
2010/0063546 A1 3/2010 Miller et al.
2010/0063547 A1 3/2010 Morin et al.
2010/0063550 A1 3/2010 Felix et al.
2010/0063552 A1 3/2010 Chin et al.
2010/0069919 A1 3/2010 Carls et al.
2010/0069969 A1 3/2010 Ampuero et al.
2010/0082066 A1 4/2010 Biyani
2010/0087858 A1 4/2010 Abdou
2010/0087862 A1 4/2010 Biedermann et al.
2010/0087863 A1 4/2010 Biedermann et al.
2010/0087864 A1 4/2010 Klein et al.
2010/0087865 A1 4/2010 Biedermann et al.
2010/0094343 A1 4/2010 Pham et al.
2010/0094348 A1 4/2010 Biedermann et al.
2010/0094349 A1 4/2010 Hammer et al.
2010/0094352 A1 4/2010 Iott et al.
2010/0094353 A1 4/2010 Shim et al.
2010/0100136 A1 4/2010 Won et al.
2010/0100137 A1 4/2010 Justis et al.
2010/0106189 A1 4/2010 Miller
2010/0106192 A1 4/2010 Barry
2010/0114165 A1 5/2010 Ely
2010/0114170 A1 5/2010 Barrus et al.
2010/0114171 A1 5/2010 Boachie-Adjei et al.
2010/0114179 A1 5/2010 Moore et al.
2010/0114180 A1 5/2010 Rock et al.
2010/0114182 A1 5/2010 Wilcox et al.
2010/0121386 A1 5/2010 Peultier et al.
2010/0125302 A1 5/2010 Hammill, Sr. et al.
2010/0137908 A1 6/2010 Zhang
2010/0137912 A1 6/2010 Alcock et al.
2010/0137918 A1 6/2010 Wilcox et al.
2010/0137920 A1 6/2010 Hammill, Sr. et al.
2010/0152776 A1 6/2010 Keyer et al.
2010/0152785 A1 6/2010 Forton et al.
2010/0160965 A1 6/2010 Viker
2010/0160967 A1 6/2010 Capozzoli
2010/0160968 A1 6/2010 Joshi et al.
2010/0160974 A1 6/2010 Viker
2010/0160976 A1 6/2010 Biedermann et al.
2010/0168796 A1 7/2010 Eliasen et al.
2010/0168800 A1 7/2010 Biedermann et al.
2010/0168801 A1 7/2010 Biedermann et al.
2010/0168803 A1 7/2010 Hestad et al.
2010/0174319 A1 7/2010 Jackson
2010/0174322 A1 7/2010 Abdelgany et al.
2010/0179602 A1 7/2010 Dauster et al.
2010/0191293 A1 7/2010 Jackson
2010/0204735 A1 8/2010 Gephart et al.
2010/0211104 A1 8/2010 Moumene et al.
2010/0211105 A1 8/2010 Moumene et al.
2010/0211114 A1 8/2010 Jackson
2010/0222822 A1 9/2010 Farris et al.
2010/0222828 A1 9/2010 Stad et al.
2010/0228292 A1 9/2010 Arnold et al.
2010/0234902 A1 9/2010 Biedermann et al.
2010/0249843 A1 9/2010 Wegzyn, III
2010/0249846 A1 9/2010 Simonson
2010/0249856 A1 9/2010 Iott et al.
2010/0262185 A1 10/2010 Gelfand et al.
2010/0262187 A1 10/2010 Marik et al.
2010/0262190 A1 10/2010 Ballard et al.
2010/0262191 A1 10/2010 Marik et al.
2010/0262192 A1 10/2010 Foley
2010/0274285 A1 10/2010 Rouleau
2010/0274287 A1 10/2010 Rouleau et al.
2010/0274288 A1 10/2010 Prevost et al.
2010/0298891 A1 11/2010 Jackson
2010/0305621 A1 12/2010 Wang et al.

(56) References Cited

U.S. PATENT DOCUMENTS

| | | | |
|---|---|---|---|
| 2010/0312288 | A1 | 12/2010 | Hammill, Sr. et al. |
| 2010/0331885 | A1 | 12/2010 | Remington et al. |
| 2011/0004256 | A1 | 1/2011 | Biedermann et al. |
| 2011/0009906 | A1 | 1/2011 | Hestad et al. |
| 2011/0009911 | A1 | 1/2011 | Hammill et al. |
| 2011/0029022 | A1 | 2/2011 | Zehnder et al. |
| 2011/0040338 | A1 | 2/2011 | Jackson |
| 2011/0046683 | A1 | 2/2011 | Biedermann et al. |
| 2011/0093015 | A1 | 4/2011 | Ramsay et al. |
| 2011/0093021 | A1 | 4/2011 | Fanger et al. |
| 2011/0106174 | A1 | 5/2011 | Rezach |
| 2011/0106175 | A1 | 5/2011 | Rezach |
| 2011/0130792 | A1 | 6/2011 | Nydegger et al. |
| 2011/0152939 | A1 | 6/2011 | Aldridge |
| 2011/0152947 | A1 | 6/2011 | Kirschman |
| 2011/0152949 | A1 | 6/2011 | Biedermann et al. |
| 2011/0160778 | A1 | 6/2011 | Elsbury |
| 2011/0166610 | A1 | 7/2011 | Altarac et al. |
| 2011/0178558 | A1 | 7/2011 | Barry |
| 2011/0178560 | A1 | 7/2011 | Butler et al. |
| 2011/0184469 | A1 | 7/2011 | Ballard et al. |
| 2011/0184471 | A1 | 7/2011 | Foley et al. |
| 2011/0190822 | A1 | 8/2011 | Spitler et al. |
| 2011/0196430 | A1 | 8/2011 | Walsh |
| 2011/0202094 | A1 | 8/2011 | Pereira et al. |
| 2011/0202095 | A1 | 8/2011 | Semler et al. |
| 2011/0208248 | A1 | 8/2011 | Barrus et al. |
| 2011/0230915 | A1 | 9/2011 | Anderson et al. |
| 2011/0238119 | A1 | 9/2011 | Moumene et al. |
| 2011/0251644 | A1 | 10/2011 | Hestad et al. |
| 2011/0257685 | A1 | 10/2011 | Hay et al. |
| 2011/0257687 | A1 | 10/2011 | Trieu et al. |
| 2011/0257689 | A1 | 10/2011 | Fiechter et al. |
| 2011/0257690 | A1 | 10/2011 | Rezach |
| 2011/0263945 | A1 | 10/2011 | Peterson et al. |
| 2011/0270321 | A1 | 11/2011 | Prevost et al. |
| 2011/0313460 | A1 | 12/2011 | Mclean et al. |
| 2011/0313463 | A1 | 12/2011 | McLean |
| 2011/0313471 | A1 | 12/2011 | McLean et al. |
| 2012/0029568 | A1 | 2/2012 | Jackson et al. |
| 2012/0029578 | A1 | 2/2012 | Suh |
| 2012/0046699 | A1 | 2/2012 | Jones et al. |
| 2012/0053636 | A1 | 3/2012 | Schmocker |
| 2012/0071928 | A1 | 3/2012 | Jackson |
| 2012/0078307 | A1 | 3/2012 | Nihalani |
| 2012/0197314 | A1 | 8/2012 | Farris |
| 2012/0232598 | A1 | 9/2012 | Hestad et al. |
| 2012/0310284 | A1 | 12/2012 | Gerchow |
| 2013/0013003 | A1 | 1/2013 | Carbone et al. |
| 2013/0103097 | A1 | 4/2013 | May et al. |
| 2013/0150852 | A1 | 6/2013 | Shluzas et al. |
| 2014/0012332 | A1 | 1/2014 | Jackson |
| 2014/0052187 | A1 | 2/2014 | McBride et al. |
| 2014/0081334 | A1 | 3/2014 | Jackson |
| 2014/0142633 | A1 | 5/2014 | Jackson et al. |
| 2014/0214097 | A1 | 7/2014 | Jackson et al. |
| 2015/0094770 | A1 | 4/2015 | Jackson et al. |
| 2015/0119942 | A1 | 4/2015 | Jackson et al. |
| 2015/0164558 | A1 | 6/2015 | Jackson et al. |
| 2016/0022320 | A1 | 1/2016 | Jackson et al. |
| 2016/0038188 | A1 | 2/2016 | Jackson et al. |
| 2016/0242818 | A1 | 8/2016 | Jackson |
| 2017/0333083 | A1 | 11/2017 | Jackson et al. |
| 2017/0340363 | A1 | 11/2017 | Jackson |
| 2017/0354441 | A1 | 12/2017 | Jackson et al. |
| 2017/0354443 | A1 | 12/2017 | Jackson |
| 2018/0243013 | A1 | 8/2018 | Jackson et al. |
| 2018/0296249 | A1 | 10/2018 | Jackson |
| 2019/0175225 | A1 | 6/2019 | Jackson et al. |
| 2019/0231400 | A1 | 8/2019 | Jackson et al. |
| 2019/0274734 | A1 | 9/2019 | Jackson et al. |
| 2020/0163702 | A1 | 5/2020 | Jackson et al. |
| 2020/0179014 | A1 | 6/2020 | Jackson |

FOREIGN PATENT DOCUMENTS

| | | | |
|---|---|---|---|
| DE | 3630863 | | 3/1988 |
| DE | G9202745.8 | | 4/1992 |
| DE | 4425392 | | 11/1995 |
| DE | 29806563 | | 6/1998 |
| DE | 29810798 | | 12/1999 |
| DE | 19951145 | | 5/2001 |
| DE | 20207850 | | 10/2002 |
| DE | 102007055745 | | 7/2008 |
| EP | 0195455 | | 9/1986 |
| EP | 0172130 | | 2/1987 |
| EP | 0276153 | | 7/1988 |
| EP | 0667127 | | 8/1995 |
| EP | 0669109 | | 8/1995 |
| EP | 0677277 | | 10/1995 |
| EP | 1277444 | | 1/2003 |
| EP | 2082709 | | 7/2009 |
| EP | 2468198 | | 12/2010 |
| ES | 2384773 | | 7/2012 |
| FR | 2467312 | | 4/1981 |
| FR | 2715825 | | 8/1995 |
| FR | 2717370 | | 9/1995 |
| FR | 2718946 | | 10/1995 |
| FR | 2799949 | | 4/2001 |
| FR | 2814936 | | 4/2002 |
| FR | 2815535 | | 4/2002 |
| FR | 2856578 | | 6/2003 |
| FR | 2865377 | | 1/2004 |
| FR | 2846223 | | 4/2004 |
| FR | 2857850 | | 4/2004 |
| FR | 2925288 | | 6/2009 |
| GB | 203508 | | 9/1923 |
| GB | 2082709 | | 3/1982 |
| GB | 2140523 | | 11/1984 |
| GB | 2140523 | A | 11/1984 |
| GB | 2365345 | | 2/2002 |
| GB | 2382304 | | 5/2003 |
| JP | S4867159 | | 9/1973 |
| JP | S50106061 | | 8/1975 |
| JP | H10277070 | | 10/1998 |
| JP | 2000325358 | | 3/2000 |
| JP | 2002052030 | | 2/2002 |
| JP | 2002221218 | | 8/2002 |
| SU | 371359 | | 2/1973 |
| WO | 8909030 | | 10/1989 |
| WO | 8912431 | | 12/1989 |
| WO | 9116018 | | 10/1991 |
| WO | 9116020 | | 10/1991 |
| WO | 9203100 | | 3/1992 |
| WO | 9321848 | | 11/1993 |
| WO | 9325161 | | 12/1993 |
| WO | 9410927 | | 5/1994 |
| WO | 9410944 | | 5/1994 |
| WO | 9426191 | | 11/1994 |
| WO | 9428824 | | 12/1994 |
| WO | 9501132 | | 1/1995 |
| WO | 9513755 | | 5/1995 |
| WO | WO 95/13755 | | 5/1995 |
| WO | 9528889 | | 11/1995 |
| WO | 9531947 | | 11/1995 |
| WO | 9535067 | | 12/1995 |
| WO | 9606576 | | 3/1996 |
| WO | 9621396 | | 7/1996 |
| WO | 9625104 | | 8/1996 |
| WO | 9628105 | | 9/1996 |
| WO | 9628118 | | 9/1996 |
| WO | 9641582 | | 12/1996 |
| WO | 9714366 | | 4/1997 |
| WO | 9714368 | | 4/1997 |
| WO | 9727812 | | 8/1997 |
| WO | 9730649 | | 8/1997 |
| WO | 9737604 | | 10/1997 |
| WO | 9737605 | | 10/1997 |
| WO | 9812977 | | 4/1998 |
| WO | 9815233 | | 4/1998 |
| WO | 9825534 | | 6/1998 |
| WO | 9832386 | | 7/1998 |
| WO | 9834554 | | 8/1998 |

(56) References Cited

FOREIGN PATENT DOCUMENTS

| | | |
|---|---|---|
| WO | 9834556 | 8/1998 |
| WO | 9838924 | 9/1998 |
| WO | 9903415 | 1/1999 |
| WO | 9905980 | 2/1999 |
| WO | 9932084 | 7/1999 |
| WO | 9938463 | 8/1999 |
| WO | 9947083 | 9/1999 |
| WO | 9949802 | 10/1999 |
| WO | 2000015125 | 3/2000 |
| WO | 2000022997 | 4/2000 |
| WO | 2000027297 | 5/2000 |
| WO | 2000072769 | 7/2000 |
| WO | 2000065268 | 11/2000 |
| WO | 2000066045 | 11/2000 |
| WO | 2001006940 | 2/2001 |
| WO | 2001008574 | 2/2001 |
| WO | 2001010317 | 2/2001 |
| WO | 2001015612 | 3/2001 |
| WO | 2001022893 | 4/2001 |
| WO | 2001028435 | 4/2001 |
| WO | 2001028436 | 4/2001 |
| WO | 2001045576 | 6/2001 |
| WO | 2001049191 | 7/2001 |
| WO | 20010058370 | 8/2001 |
| WO | 2001067972 | 9/2001 |
| WO | 2001067974 | 9/2001 |
| WO | 2002022030 | 3/2002 |
| WO | 2002034150 | 5/2002 |
| WO | 2002054966 | 7/2002 |
| WO | 2002102259 | 12/2002 |
| WO | 2003007828 | 1/2003 |
| WO | 2003026523 | 4/2003 |
| WO | 2003037199 | 5/2003 |
| WO | 2003047442 | 6/2003 |
| WO | 2003068083 | 8/2003 |
| WO | 2003068088 | 8/2003 |
| WO | 2003084415 | 10/2003 |
| WO | 2003094699 | 11/2003 |
| WO | 2004021900 | 3/2004 |
| WO | 2004022108 | 3/2004 |
| WO | 2004041100 | 5/2004 |
| WO | 2004075778 | 9/2004 |
| WO | 2004089245 | 10/2004 |
| WO | 2004098452 | 11/2004 |
| WO | 2004105577 | 12/2004 |
| WO | 2004107997 | 12/2004 |
| WO | 2005000136 | 1/2005 |
| WO | 2005000137 | 1/2005 |
| WO | 2005013839 | 2/2005 |
| WO | 2005018466 | 3/2005 |
| WO | 2005018471 | 3/2005 |
| WO | 2005020829 | 3/2005 |
| WO | 2005030068 | 4/2005 |
| WO | 2005065374 | 7/2005 |
| WO | 2005072632 | 8/2005 |
| WO | 2005082262 | 9/2005 |
| WO | 2005087121 | 9/2005 |
| WO | 2005099400 | 10/2005 |
| WO | 2005102195 | 11/2005 |
| WO | 2005104969 | 11/2005 |
| WO | 2006005198 | 1/2006 |
| WO | 2006017616 | 2/2006 |
| WO | 2006020530 | 2/2006 |
| WO | 2006042188 | 4/2006 |
| WO | 2006047711 | 5/2006 |
| WO | 2006054111 | 5/2006 |
| WO | 2006065607 | 6/2006 |
| WO | 2006066685 | 6/2006 |
| WO | 2006068711 | 6/2006 |
| WO | 2006071742 | 7/2006 |
| WO | 2006079531 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | 2006116437 | 11/2006 |
| WO | 2006119447 | 11/2006 |
| WO | 2007002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007053566 | 5/2007 |
| WO | 2007060534 | 5/2007 |
| WO | 2007075454 | 7/2007 |
| WO | 2007081849 | 8/2007 |
| WO | 2007087469 | 8/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007109470 | 9/2007 |
| WO | 2007114834 | 10/2007 |
| WO | 2007118045 | 10/2007 |
| WO | 2007121030 | 10/2007 |
| WO | 2007121057 | 10/2007 |
| WO | 2007121271 | 10/2007 |
| WO | 2007123920 | 11/2007 |
| WO | 2007124222 | 11/2007 |
| WO | 2007124249 | 11/2007 |
| WO | 2007127595 | 11/2007 |
| WO | 2007127604 | 11/2007 |
| WO | 2007130835 | 11/2007 |
| WO | 2007130840 | 11/2007 |
| WO | 2007130941 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008008511 | 1/2008 |
| WO | 2008013892 | 1/2008 |
| WO | 2008027860 | 3/2008 |
| WO | 2008033742 | 3/2008 |
| WO | 2008036975 | 3/2008 |
| WO | 2008037256 | 4/2008 |
| WO | 2008039777 | 4/2008 |
| WO | 2008042948 | 4/2008 |
| WO | 2008048923 | 4/2008 |
| WO | 2008048953 | 4/2008 |
| WO | 2008051737 | 4/2008 |
| WO | 2008069420 | 6/2008 |
| WO | 2008070716 | 6/2008 |
| WO | 2008134703 | 6/2008 |
| WO | 2008078163 | 7/2008 |
| WO | 2008082737 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008140756 | 11/2008 |
| WO | 2008157589 | 12/2008 |
| WO | 2009003153 | 12/2008 |
| WO | 2009006225 | 1/2009 |
| WO | 2009011845 | 1/2009 |
| WO | 2009014540 | 1/2009 |
| WO | 2009015100 | 1/2009 |
| WO | 2009018086 | 2/2009 |
| WO | 2009029928 | 3/2009 |
| WO | 2009055028 | 4/2009 |
| WO | 2009055400 | 4/2009 |
| WO | 2009055407 | 4/2009 |
| WO | 2009152302 | 12/2009 |
| WO | 2009155360 | 12/2009 |
| WO | 2010017631 | 2/2010 |
| WO | 2010018316 | 2/2010 |
| WO | 2010018317 | 2/2010 |
| WO | 2010019857 | 2/2010 |
| WO | 2010030916 | 3/2010 |
| WO | 2010045383 | 4/2010 |
| WO | 2010065648 | 6/2010 |
| WO | 2010078901 | 7/2010 |
| WO | 2010111500 | 9/2010 |
| WO | 2010120989 | 10/2010 |

(56) References Cited

FOREIGN PATENT DOCUMENTS

| | | |
|---|---|---|
| WO | 2010147639 | 12/2010 |
| WO | 2011043805 | 4/2011 |
| WO | 2011068818 | 6/2011 |
| WO | 2012033532 | 3/2012 |
| WO | 2012075827 | 6/2012 |
| WO | 2012088890 | 7/2012 |

OTHER PUBLICATIONS

CD Horizon M8 Multi Axial Screw Spinal System Brochure, Medtronic Sofamor Danek, no publish date.
Claris Instrumentation Brochure, G Med, pub. 1997.
Contour Spinal System Brochure, Ortho Development, no publish date.
EBI Omega 21 Brochure, EBI Spine Systems, pub. 1999.
SDRS Surgical Dynamics Rod System Brochure, Surgical Dynamics, pub. 1998-1999
Silhouette Spinal Fixation System Brochure, Sulzer Medica Spine-Tech, no publish date.
Spine, Lipcott, Williams & Wilkins, Inc. vol. 24, No. 15, p. 1495.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.
Brochure of DePuySpine on Surgical Technique, Published 2004, pp. 1-36.
U.S. Appl. No. 15/852,866, filed Dec. 22, 2017, Jackson et al.
U.S. Appl. No. 15/883,993, filed Jan. 30, 2018, Jackson.
U.S. Appl. No. 16/391,049, filed Apr. 22, 2019, Jackson et al.
European Search Report, EP14189707.4, dated Feb. 25, 2015.

* cited by examiner 110
118
117
118
18
106
115
114
108
111
21
92
90
12
104
52
74
6.
54
10
6.
64
75
50
72
78
73
A
42
44
38
40
8
36
34
26
32
6
4
24
1
28

98
99
12
90
3.
3.
92

99
C
102
92
12
H
104
98
96
94

32
38
45
34
8
5.
5.
42
48
40
44

57
62
56
68
69
64
65
40
42
80
10
38
78
102
36
82
86
12
83
94
8
26
37
32

A 31
10
69
40
65
118
68
82
64
119
26
6
120
38
12
32
24
15
28

60
62
116
60
52
54
10
106
21
68
69
56
64
65
80
50
83
40
86
8
12
26
32
24
6
15

52
116
108
21
18
111
54
106
65
10
50
4
6
24
28

284
288
286
296
294
212
296
285
260
17.
262
260
254
252
265
17.
270
276
280
250
278
244
A'
248
242
208
238
236
234
232
204
206
224
201
228
246

94
296
298
284
286
282
288
14.
14.
300
212
296

284
296
C
286
288
298
294
212
292
290
300
285

245
236
208
244
16.
16.
234
248
242

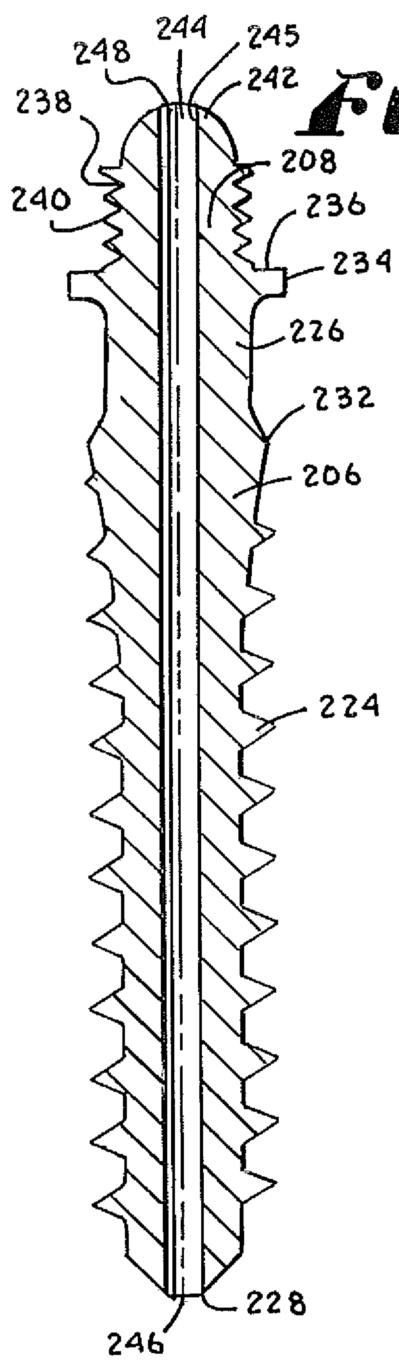
Fig.16.
244
245
248
242
238
208
240
236
234
226
232
206
224
228
246
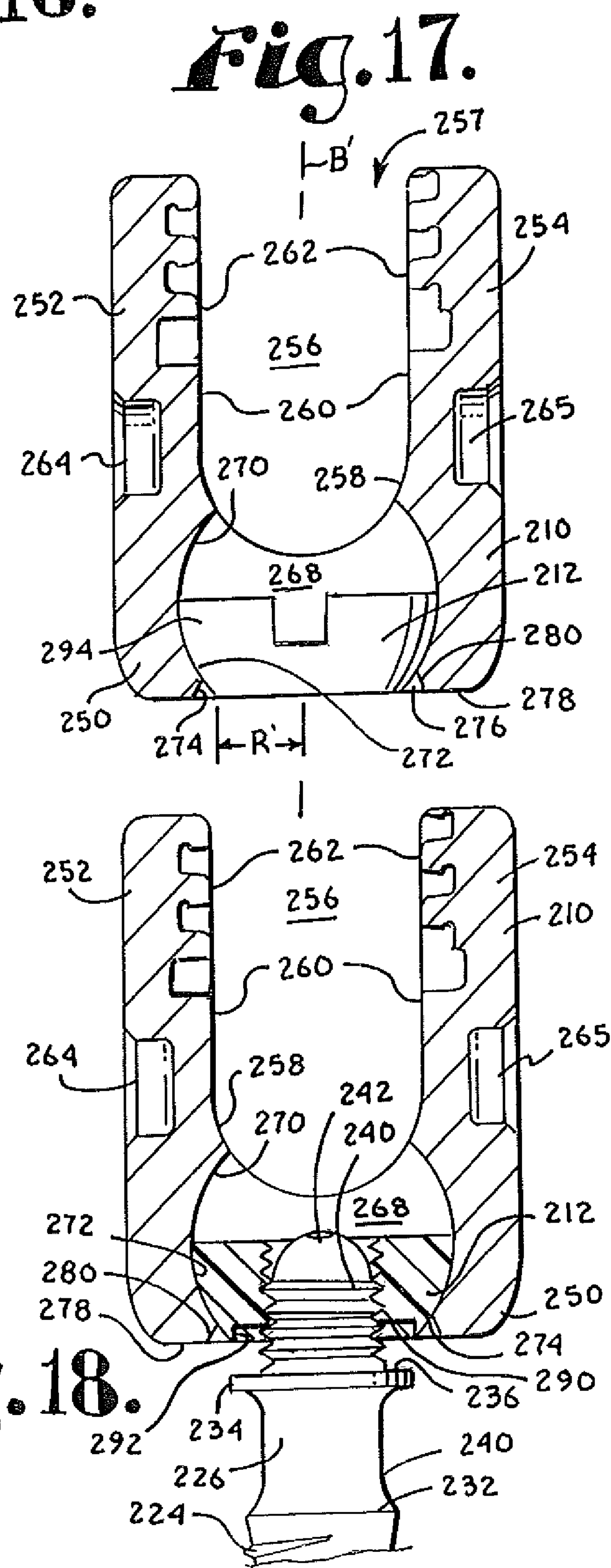
Fig.17.
B'
257
262
254
252
256
260
265
264
270
258
210
268
212
280
294
278
250
276
274
R'
272
Fig.18.
262
252
254
256
210
260
264
265
258
242
270
240
268
272
212
280
250
278
274
290
236
292
234
240
226
232
224

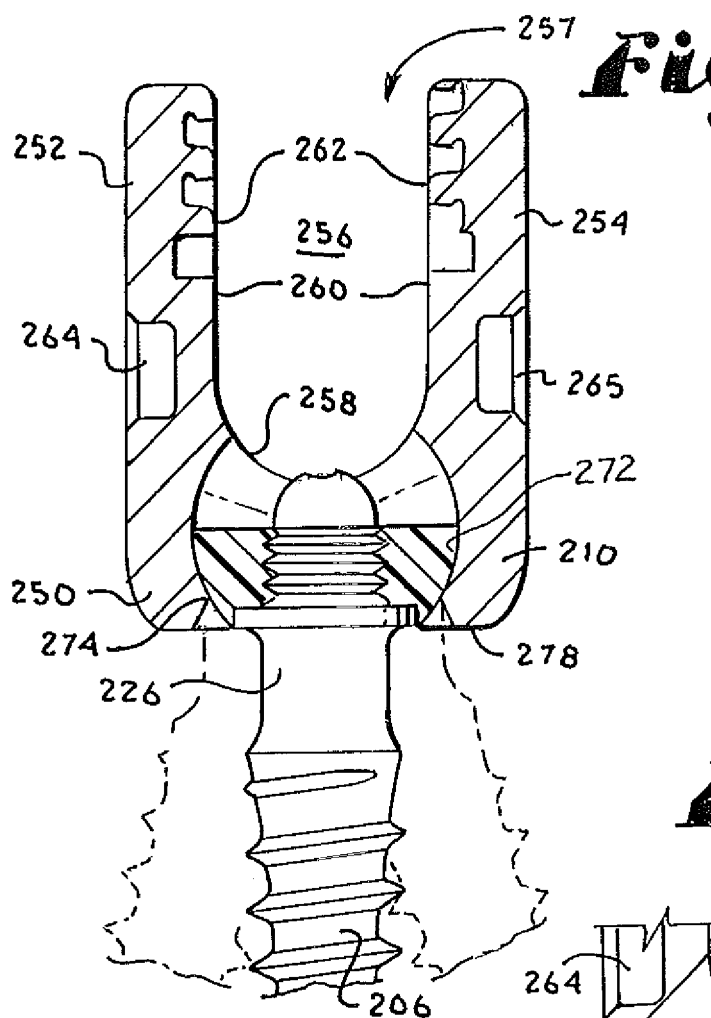
Fig. 19.
Fig. 20.
244
242
304
210
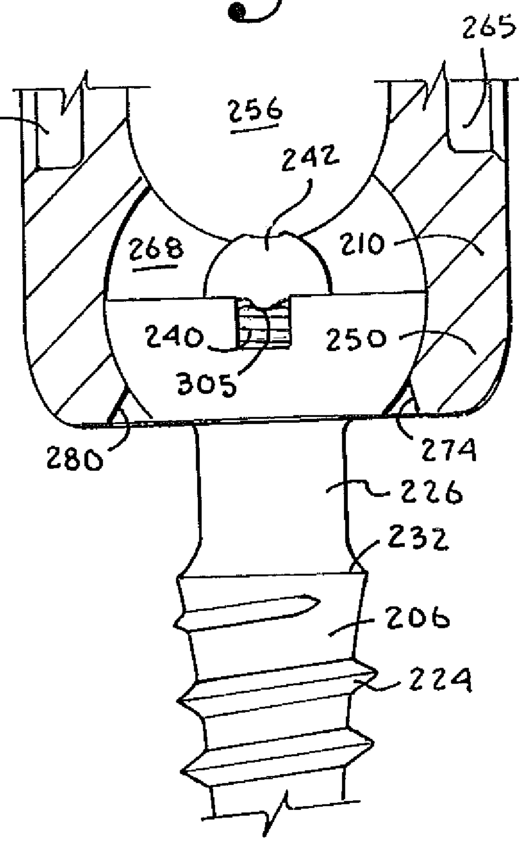
Fig. 21.

231
242
302
302
274
278
226
206
215
224
228
320
312
318
314
218
310
319
316
257
254
306'
221
252
258
210
226
206
224
215

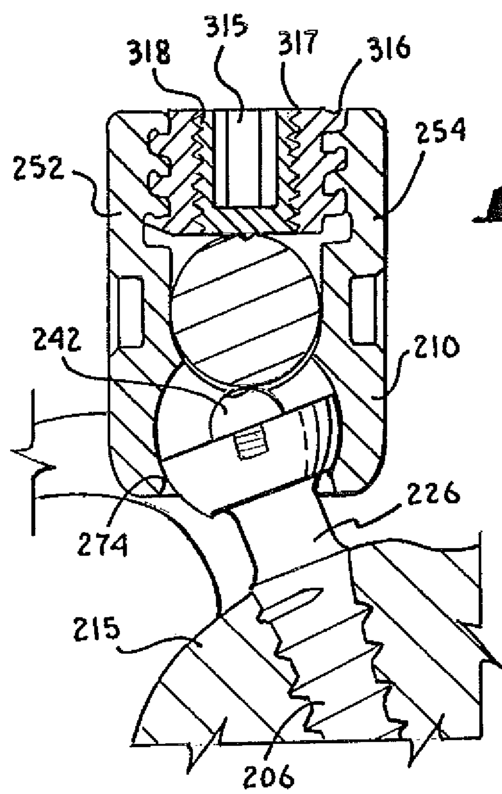
Fig.24.
Fig.25.
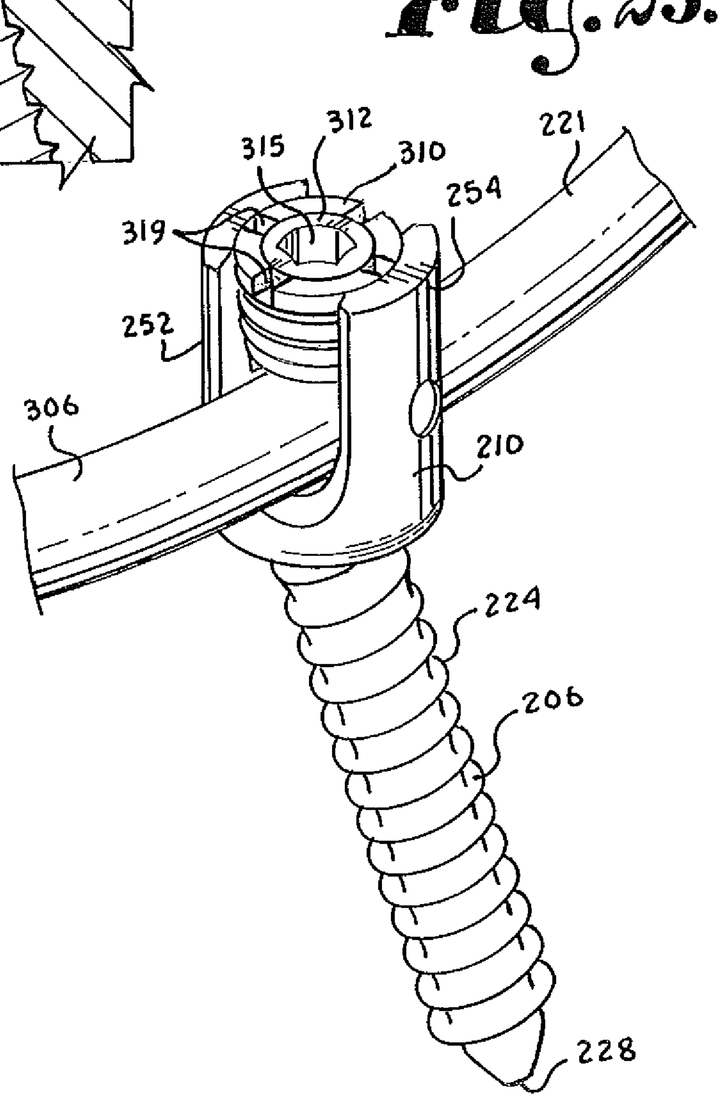

PIVOTAL BONE ANCHOR RECEIVER ASSEMBLY WITH THREADED CLOSURE

CROSS REFERENCE TO RELATED APPLICATION

This application is a continuation of application of U.S. patent application Ser. No. 13/896,490, filed May 17, 2013, now U.S. Pat. No. 8,998,960, which is a continuation of application Ser. No. 12/807,937, filed Sep. 17, 2010, now U.S. Pat. No. 8,444,677, which is a continuation of application Ser. No. 10/986,377, filed Nov. 10, 2004, now U.S. Pat. No. 7,833,250, each of which are incorporated herein by reference.

BACKGROUND OF THE INVENTION

The present invention is directed to polyaxial bone screws for use in bone surgery, particularly spinal surgery. Such screws have a head that can swivel about a shank of the bone screw, allowing the head to be positioned in any of a number of angular configurations relative to the shank.

Many spinal surgery procedures require securing various implants to bone and especially to vertebrae along the spine. For example, elongate rods are often utilized that extend along the spine to provide support to vertebrae that have been damaged or weakened due to injury or disease. Such rods must be supported by certain vertebrae and support other vertebrae.

The most common mechanism for providing vertebral support is to implant bone screws into certain bones which then in turn support the rod or are supported by the rod. Bone screws of this type may have a fixed head relative to a shank thereof. In the fixed bone screws, the head cannot be moved relative to the shank and the rod must be favorably positioned in order for it to be placed within the head. This is sometimes very difficult or impossible to do. Therefore, polyaxial bone screws are commonly preferred.

Polyaxial bone screws allow rotation of the head about the shank until a desired rotational position of the head is achieved relative to the shank. Thereafter, a rod can be inserted into the head and eventually the head is locked or fixed in a particular position relative to the shank.

A variety of polyaxial or swivel-head bone screw assemblies are available. One type of bone screw assembly includes an open head that allows for placement of a rod within the head. A closure top or plug is then used to capture the rod in the head of the screw.

Because such implants are for placement within the human body, it is desirable for the implant to have as little effect on the body as possible. Consequently, heavy, bulky implants are undesirable and lighter implants with a relatively small profile both in height and width are more desirable. However, a drawback to smaller, lighter implants is that they may be more difficult to rigidly fix to each other and into a desired position. Lack of bulk may also mean lack of strength, resulting in slippage under high loading. Also, more component parts may be required to rigidly fix the implant in a desired position. A further drawback of smaller components is that they may be difficult to handle during surgery because of their small size, failing to provide adequate driving or gripping surfaces for tools used to drive the shank into bone.

One undesirable attribute of some of the swivel-head implants is the need for a multitude of components that may loosen or even disassemble within the body. It is most undesirable for components to be free to move around in the body after the completion of surgery. Loosening of components relative to each other may result in related undesirable movement of the bone or vertebra that the implant was intended to stabilize.

SUMMARY OF THE INVENTION

It is an object of the invention to overcome one or more of the problems described above. Further objects of the invention include: providing a polyaxial bone screw with features that provide adequate frictional or gripping surfaces for bone implantation tools and may be readily, securely fastened to each other and to bone. Also, if the implant should slip or become loose for some reason, an object of the invention is to provide an implant wherein all of the parts remain together and do not separate.

Furthermore, it is an object of the invention to provide a lightweight, low profile polyaxial bone screw that assembles in such a manner that the components cooperate to create an overall structure that prevents unintentional disassembly.

A polyaxial bone screw assembly of the present invention includes a shank having a body for fixation to a bone. Integral with the shank and extending axially upwardly and outwardly therefrom is a capture structure. The capture structure has a radially projecting outer surface that is substantially cylindrical and that further includes a helically wound structure, such as a thread. The upper end of the shank is convexly curved.

The bone screw assembly further includes a head having a top portion and a base. The top portion is open and has a channel. The base also is upwardly open and includes an inner seating surface partially defining a cavity and has a lower aperture or opening. The channel of the top portion communicates with the cavity, which in turn communicates with an exterior of the base of the head through the base opening. The base opening is sized and shaped to receive the capture structure of the shank into the head cavity.

The bone screw assembly also includes an integral one piece contiguously closed ring-like retainer structure that has an internal surface with a helically wound structure thereon, such as a thread. The thread of the retainer structure is sized and shaped to mate with the thread of the shank capture structure when the retainer structure and the capture structure are coaxially aligned within the head cavity, thereby securing the retainer structure to the capture structure.

The external surface of the retainer structure is configured to be in slidable mating engagement with the surface defining the cavity of the head. Preferably, the retainer structure external surface and the mating head inner surface are substantially spherical. However, it is noted that the mating surfaces may be of another shape, such as conical or tapered, especially for the head cavity inner surface. The cooperating shapes of the retainer external surface and the head inner surface enable selective angular positioning of the shank body with respect to the head.

In one embodiment according to the invention, the capture structure includes a tool engagement formation that extends or projects from the capture structure and is located between the curved upper end and the threaded cylindrical portion thereof. In another embodiment of the invention, the closed ring-like retainer structure includes a tool engagement formation. In both embodiments, the tool formation is for non-slip engagement by a tool for driving the shank into bone and may also be cooperatively used for attaching the retainer structure to the capture structure.

Also according to the invention are tool seating surfaces that may be disposed on one or both of the capture structure and the retainer structure. In one embodiment, the shank capture structure includes tool engagement surfaces that are positioned and shaped to receive a socket type tool and a planar, tool seating surface extending radially from the lower end of the tool engagement surfaces. The seating surface is disposed coaxially with the shank body. The retainer structure has mating seating surfaces that cooperate with the shank capture structure seating surface. The tool seating surfaces and the tool engagement surfaces partially define a recess for receiving a driving tool mating with the tool engagement surfaces. When engaged, the driving tool is in contact with the capture structure tool seating surface, providing greater mating surface to the capture structure tool engagement surfaces so as to provide additional surface for frictional gripping when the shank body is driven into bone, especially harder bone.

In certain embodiments a tool seating and partially surrounding surface may be disposed on the retainer structure according to the invention such that when the retainer structure is mated with the capture structure, the retainer structure seating surface extends radially from the lower end of the tool engagement surfaces and is disposed coaxially with respect to the shank body.

In certain embodiments, both the capture structure and the retainer structure may include tool seating surfaces that extend radially in the same plane when the capture structure and the retainer structure are mated. In such embodiments, the two tool seating surfaces and the shank tool engagement surfaces partially define a recess for receiving a driving tool engaged with the tool engagement surfaces. When engaged, the driving tool is in contact with both tool seating surfaces, thereby seating the tool lower relative to the tool engagement surfaces and providing additional frictional gripping surface when the shank body is driven into bone.

A polyaxial bone screw assembly method according to the invention includes inserting an independent closed ring-like retainer into a head cavity, inserting a capture structure of a bone screw shank through a shank receiving opening of the head and into a cavity thereof; and attaching the capture structure to the retainer structure within the head.

A method according to the invention further includes driving the shank body into bone by rotating the shank body with a tool engaged with a tool engagement formation, such as a pair of aligned and spaced slots, disposed on the capture structure or the retainer structure. Further assembly steps according to the invention include inserting a rod into the channel; and biasing the rod against a top of the bone screw shank capture structure by rotatably inserting a closure member structure within or onto a mating structure of the rod receiving channel structure.

It is to be understood that while certain forms of the present invention have been illustrated and described herein, it is not to be limited to the specific forms or arrangement of parts described and shown.

Other objects and advantages of this invention will be apparent to those skilled in the art from the following description taken in conjunction with the drawings and the appended claims.

The drawings constitute a part of this specification and include exemplary embodiments of the present invention and illustrate various objects and features thereof.

BRIEF DESCRIPTION OF THE DRAWINGS

FIG. 16 is an enlarged cross-sectional view of the shank of FIG. 12, taken along line 16-16 of FIG. 15.

FIG. 17 is an enlarged cross-sectional view of the head of FIG. 12 showing the retainer structure seated in the head, taken along line 17-17 of FIG. 12.

FIG. 18 is an enlarged cross-sectional view of the head and retainer structure similar to FIG. 17, showing the shank capture structure partially assembled with respect to the retainer structure.

FIG. 19 is an enlarged cross-sectional view of the head and retainer structure, similar to FIG. 18, illustrating the shank and retainer structure being pivotable to selected angles relative to the head in solid and phantom lines.

FIG. 20 is an enlarged and fragmentary perspective view, similar to FIG. 19, illustrating the use of a punch tool to lock the position of the retainer structure relative to the capture structure.

FIG. 21 is an enlarged and partial view similar to FIG. 20 showing a thread of the capture structure deformed to rigidly secure the retainer structure to the capture structure.

FIG. 24 is an enlarged cross-sectional view of the assembly of FIG. 23 shown completely assembled.

FIG. 25 is an enlarged perspective view of the assembly of FIG. 23 shown completely assembled.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 7:
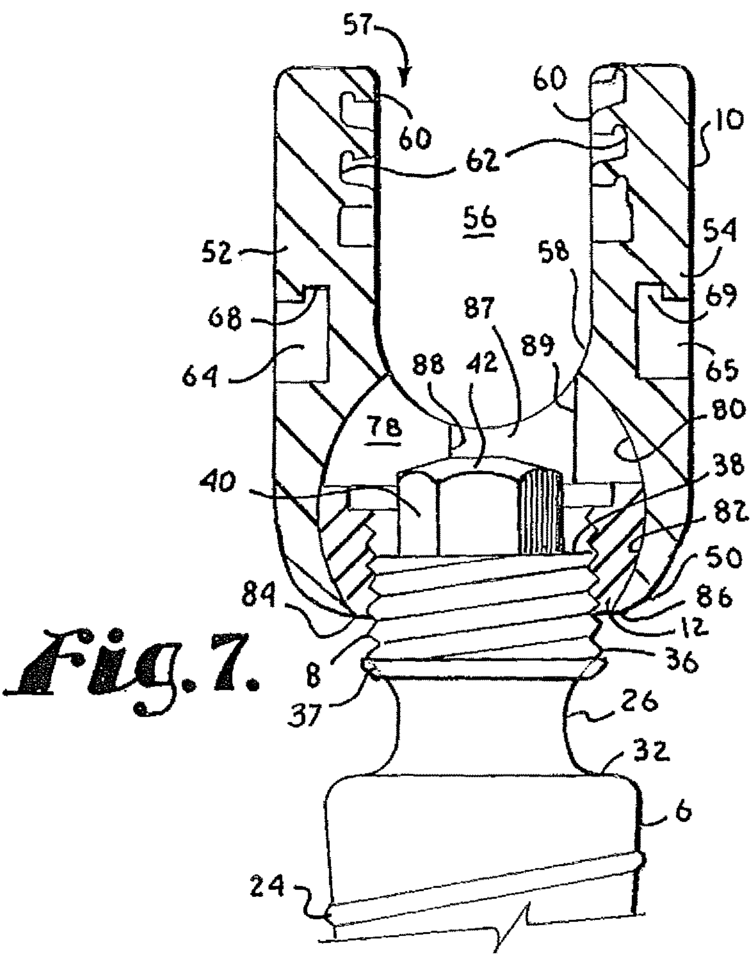
FIG. 7 is an enlarged cross-sectional view of the head and retainer structure similar to FIG. 6, showing the shank capture structure partially threaded into the retainer structure.
Figure 8:
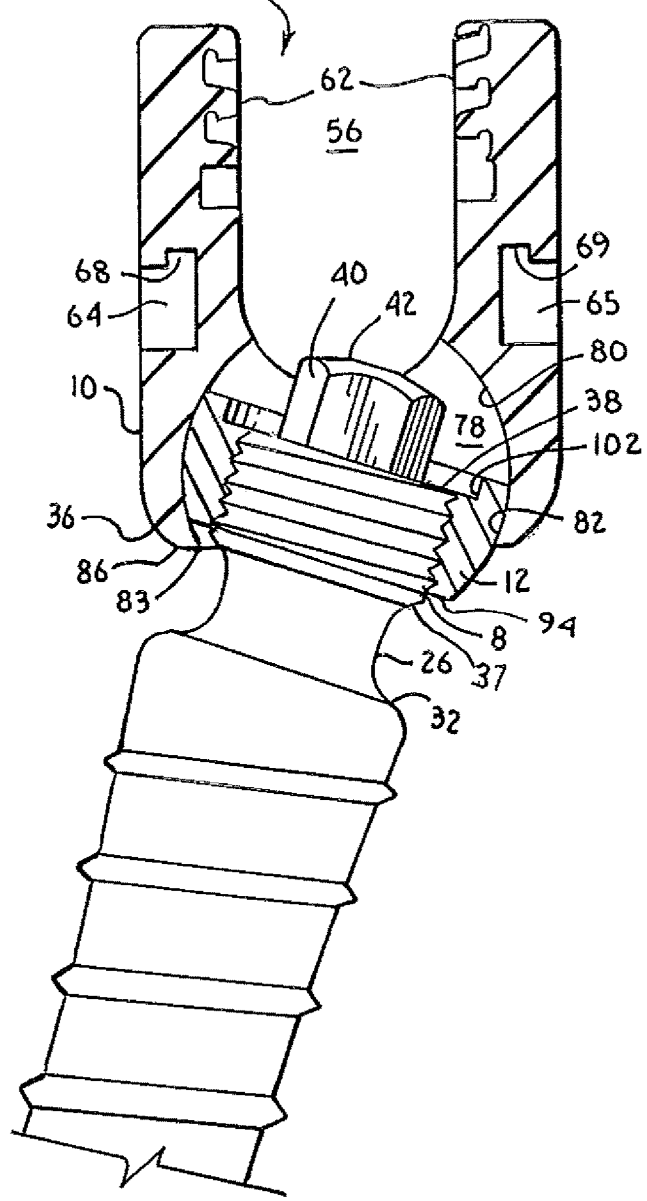
FIG. 8 is an enlarged cross-sectional view of the head and retainer structure similar to FIG. 7, illustrating the fully assembled shank and retainer structure pivoted to a selected angle relative to the head.
Figure 9:
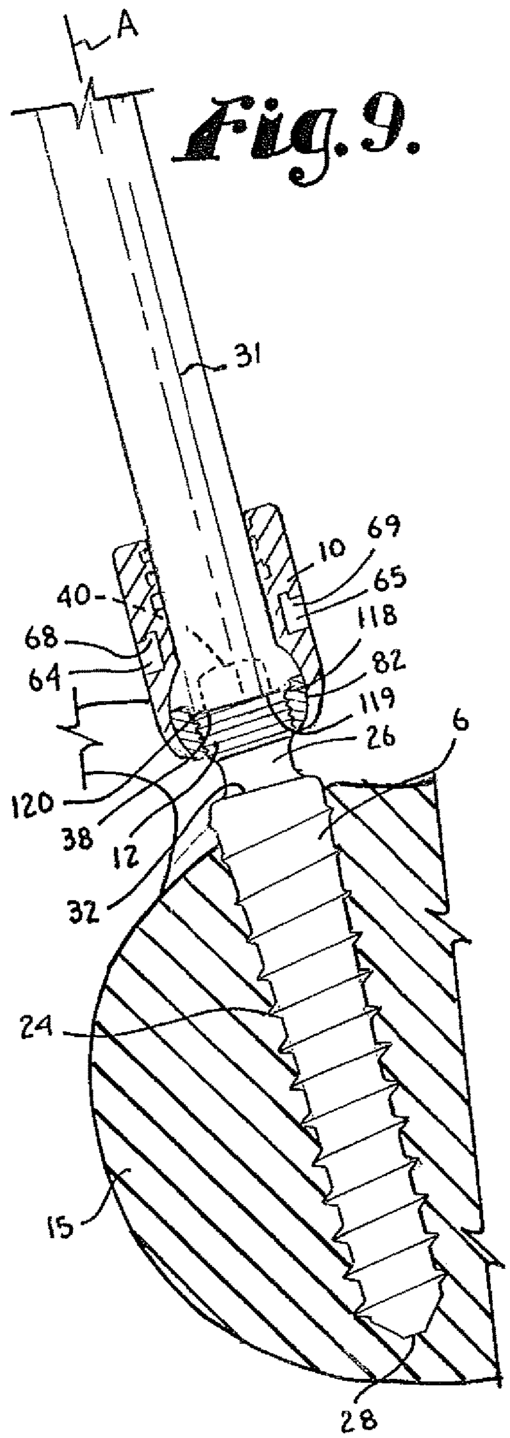
FIG. 9 is an enlarged cross-sectional view of a vertebra, and head and retainer similar to FIG. 7, showing the shank being implanted into the vertebra using a driving tool mounted on the shank capture structure.

In FIGS. 1-11 the reference number 1 generally represents a first embodiment of a polyaxial bone screw apparatus or assembly according to the present invention. The assembly 1 includes a shank 4 that further includes a body 6 integral with an upwardly extending capture structure 8; a head 10; and a closed integral retainer structure or ring 12. The shank 4, head 10 and retainer structure 12 preferably are assembled prior to implantation of the shank body 6 into a vertebra 15, which procedure is shown in FIG. 9.

Figure 1:
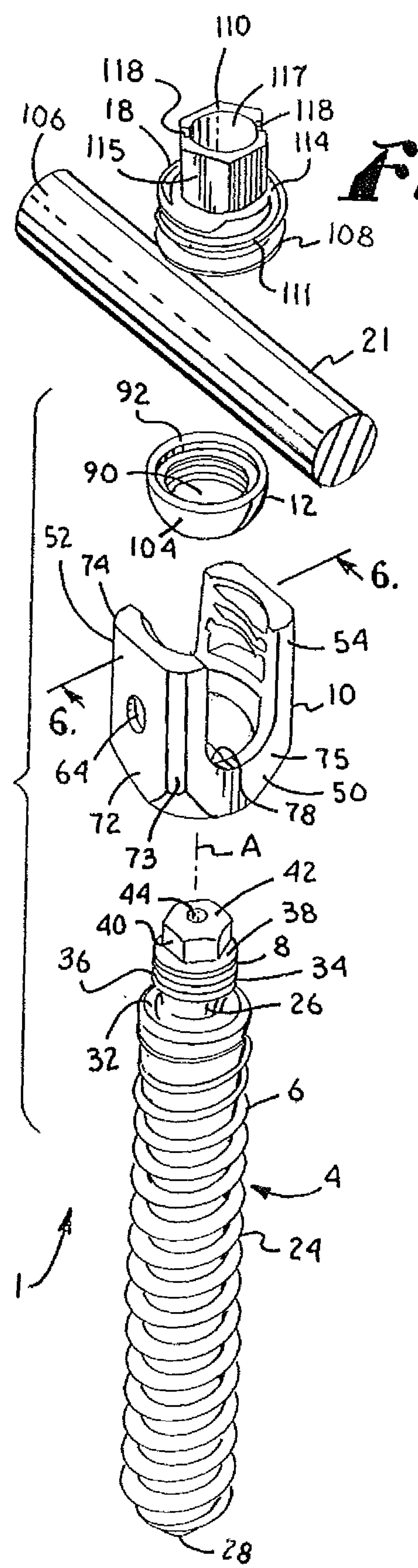
FIG. 1 is an exploded perspective view of a polyaxial bone screw assembly according to the present invention having a shank with a capture structure at one end thereof, a head, and a closed ring-like retainer structure and further showing a rod and closure structure.
Figure 2:
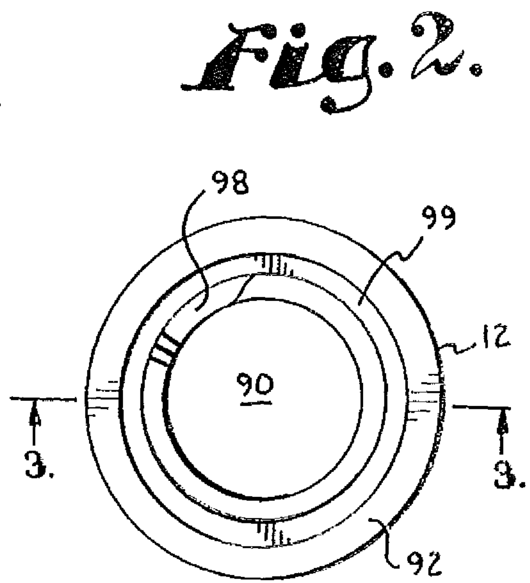
FIG. 2 is an enlarged top plan view of the retainer structure of FIG. 1.

FIG. 1 further shows a closure structure 18 of the invention for biasing a longitudinal member such as a rod 21 against the capture structure 8 which biases the ring 12 into fixed frictional contact with the head 10, so as to fix the rod 21 relative to the vertebra 15. The head 10 and shank 4 cooperate in such a manner that the head 10 and shank 4 can be secured at any of a plurality of angles, articulations or rotational alignments relative to one another and within a selected range of angles both from side to side and from front to rear, to enable flexible or articulated engagement of the head 10 with the shank 4 until both are locked or fixed relative to each other near the end of an implantation procedure.

Figure 5:
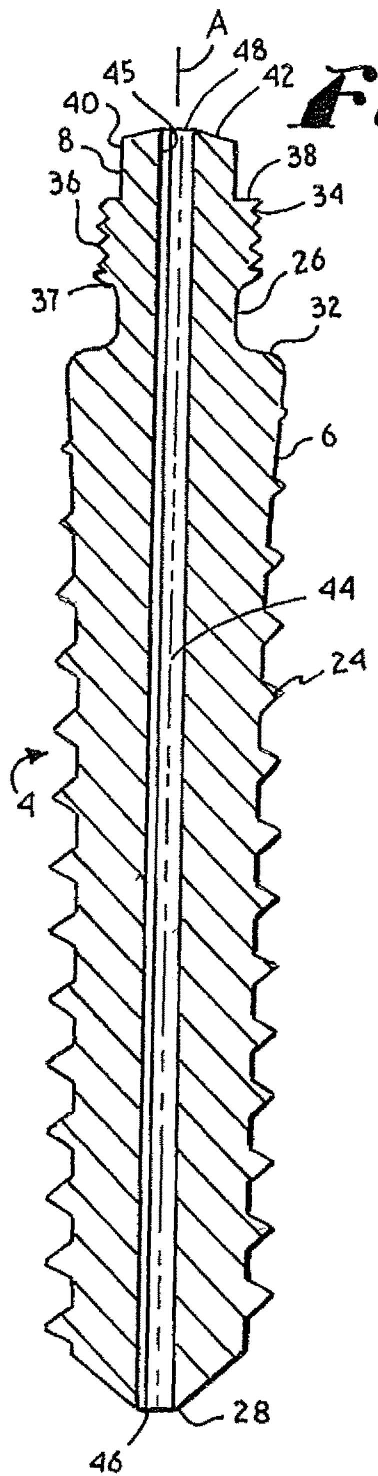
FIG. 5 is an enlarged cross-sectional view of the shank, taken along line 5-5 of FIG. 4.

The shank 4, best illustrated in FIGS. 1 and 5, is elongate, with the shank body 6 having a helically wound bone implantable thread 24 extending from near a neck 26 located adjacent to the capture structure 8 to a tip 28 of the body 6 and extending radially outward therefrom. During use, the body 6 utilizing the thread 24 for gripping and advancement is implanted into the vertebra 15 leading with the tip 28 and driven down into the vertebra 15 with an installation or driving tool 31, so as to be implanted in the vertebra 15 to near the neck 26, as shown in FIG. 9, and as is described more fully in the paragraphs below. The shank 4 has an elongate axis of rotation generally identified by the reference letter A. It is noted that any reference to the words top, bottom, up and down, and the like, in this application refers to the alignment shown in the various drawings, as well as the normal connotations applied to such devices, and is not intended to restrict positioning of the assembly 1 in actual use.

The neck 26 extends axially outward and upward from the shank body 6. The neck 26 is of reduced radius as compared to an adjacent top 32 of the body 6. Further extending axially and outwardly from the neck 26 is the capture structure 8 that provides a connective or capture apparatus disposed at a distance from the body top 32 and thus at a distance from the vertebra 15 when the body 6 is implanted in the vertebra 15.

The capture structure 8 is configured for connecting the shank 4 to the head 10 and capturing the shank 4 in the head 10. The capture structure 8 has an outer substantially cylindrical surface 34 having a helically wound advancement structure thereon which in the illustrated embodiment is a V-shaped thread 36 disposed adjacent to a seating surface 38 and extending to a location near a rim 37. The rim 37 is adjacent to the neck 26. Although a simple thread 36 is shown in the drawings, it is foreseen that other structures including other types of threads, such as buttress and reverse angle threads, and non threads, such as helically wound flanges with interlocking surfaces, may be alternatively used in alternative embodiments of the present invention. The cylindrical surface 34 could be truncated giving a non-contiguous helically wound structure.

The shank 4 further includes a tool engagement structure 40 disposed near a top end surface 42 thereof for engagement of the driving tool 31 shown in FIG. 9 which includes a driving structure in the form of a socket. The tool 31 is configured to fit about the tool engagement structure 40 so as to form a socket and mating projection for both driving and rotating the shank body 6 into the vertebra 15. Specifically in the embodiment shown in FIGS. 1-11, the tool engagement structure 40 is in the shape of a hexagonally shaped extension head coaxial with both the threaded shank body 6 and the threaded capture structure 8.

Figure 10:
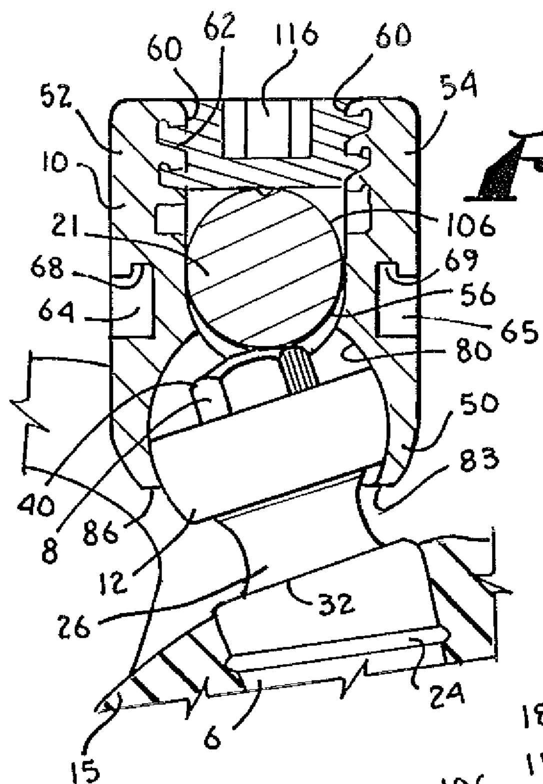
FIG. 10 is an enlarged, fragmentary cross-sectional view of the head, rod and vertebra, similar to FIG. 8 and further showing the closure member structure in contact with the rod and the rod in contact with the capture structure.
Figure 11:
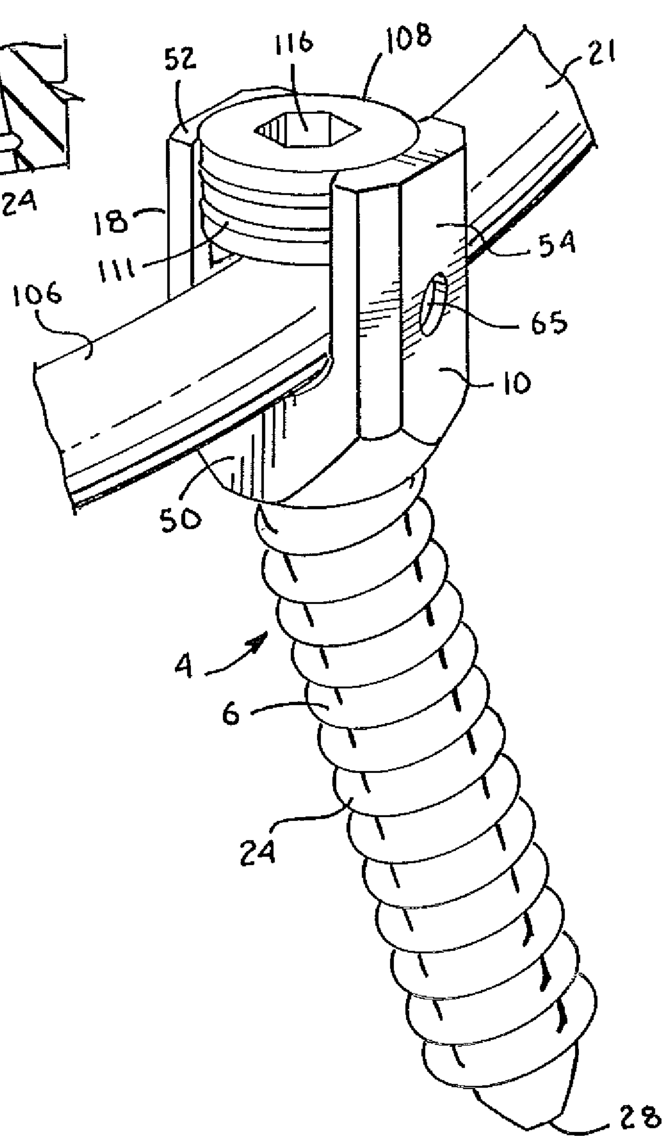
FIG. 11 is a fragmentary and enlarged perspective view of the assembly of FIG. 1 shown completely assembled.

The top end surface 42 of the shank 4 is preferably curved or dome-shaped as shown in the drawings, for contact engagement or positive mating engagement with the rod 21, when the bone screw assembly 1 is assembled, as shown in FIGS. 10 and 11 and in any alignment of the shank 4 relative to the head 10. In certain embodiments, the surface 42 is smooth. While not required in accordance with practice of the invention, the surface 42 may be scored or knurled to further increase frictional positive mating engagement between the surface 42 and the rod 21.

The shank 4 shown in the drawings is cannulated, having a small central bore 44 extending an entire length of the shank 4 along the axis A. The bore 44 is defined by an inner cylindrical wall 45 of the shank 4 and has a first circular opening 46 at the shank tip 28 and a second circular opening 48 at the top surface 42. The bore 44 is coaxial with the threaded body 6 and the capture structure outer surface 34. The bore 44 provides a passage through the shank 4 interior for a length of wire (not shown) inserted into the vertebra 15 prior to the insertion of the shank body 6, the wire providing a guide for insertion of the shank body 6 into the vertebra 15.

Referring to FIGS. 1 and 6 through 10, the head 10 has a generally U-shaped appearance with a partially cylindrical inner profile and a faceted outer profile; however, the outer profile could also be partially cylindrical. The head 10 includes a somewhat spherical base 50 integral with a pair of upstanding arms 52 and 54 forming a U-shaped cradle and defining a U-shaped channel 56 between the arms 52 and 54 with an upper opening 57 and a lower seat 58 having substantially the same radius as the rod 21 for operably snugly receiving the rod 21.

Each of the arms 52 and 54 has an interior surface 60 that defines the inner cylindrical profile and includes a partial helically wound guide and advancement structure 62. In the illustrated embodiment, the guide and advancement structure 62 is a partial helically wound interlocking flangeform configured to mate under rotation with a similar structure on the closure top 18, as described more fully below. However, it is foreseen that the guide and advancement structure 62 could alternatively be a V-shaped thread, a buttress thread, a reverse angle thread or other thread like or non-thread like helically wound advancement structures for operably guiding under rotation and advancing the closure top downward between the arms 52 and 54.

Tool engaging apertures 64 and 65 are formed within the arms 52 and 54, respectively which may be used for holding the head 10 during assembly with the shank 4 and the retainer structure 12 and also during the implantation of the shank body 6 into a vertebra 15.

Communicating with the apertures 64 and 65 are respective upwardly projecting, hidden inner recesses 68 and 69. The holding tool (not shown) is sized and shaped to have structure to mate with and to be received in the apertures 64 and 65 and locked into place by pulling the holding tool slightly axially upward relative to the base 50 and toward the upper opening 57 of the channel 56 formed by the arms 52 and 54. The holding tool and respective apertures 64 and 65 can be configured for a flexible snap on/spring off engagement wherein the holding tool has flexible legs which splay outwardly to position the tool for engagement in the apertures 64 and 65. It is noted that the apertures 64 and 65 and the cooperating holding tool may be configured to be of a variety of sizes and locations along any of the surfaces of the arms 52 and 55, for example, extending into a face 75 or disposed only at a single face or facet.

Communicating with and located beneath the U-shaped channel 56 of the head 10 is a chamber or cavity 78 substantially defined by an inner surface 80 of the base 50, the cavity 78 opens upwardly into the U-shaped channel 56. The inner surface 80 is substantially spherical, with at least a portion thereof forming a partial internal spherical seating surface 82 having a first radius. The surface 82 is sized and shaped for mating with the retainer structure 12, as described more fully below.

The base 50 further includes a restrictive neck 83, having a second radius R and defining a bore 84 communicating with the cavity 78 and a lower exterior 86 of the base 50. The bore 84 is coaxially aligned with respect to a rotational axis B of the head 10. The neck 83 and associated bore 84 are sized and shaped to be smaller (the second radius) than a radial dimension of the retainer structure 12 (the first radius), as will be discussed further below, so as to form a restriction at the location of the neck 83 relative to the retainer structure 12, to prevent the retainer structure 12 from passing from the cavity 78 and out into the lower exterior 86 of the head 10 when the retainer structure 12 is seated.

The inner surface 80 further defines an elongate upper loading recess 87 for accommodating and loading the retainer structure 12 into the cavity 78. The loading recess 87 is generally vertically disposed in the head 10, extending between and communicating with both the channel 56 and the cavity 78, allowing for ease in top loading the retainer structure 12 into the cavity through the upper opening 57 and otherwise allowing for the spherical wall 80 of the head 10 to have a comparatively enlarged radius to allow for increased thickness and strength of the head base 50; however, the loading recess 87 is not always necessary.

Figure 3:
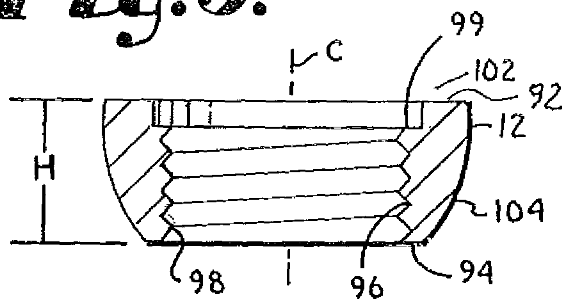
FIG. 3 is an enlarged cross-sectional view of the retainer structure of FIG. 2, taken along line 3-3 of FIG. 2.
Figure 4:
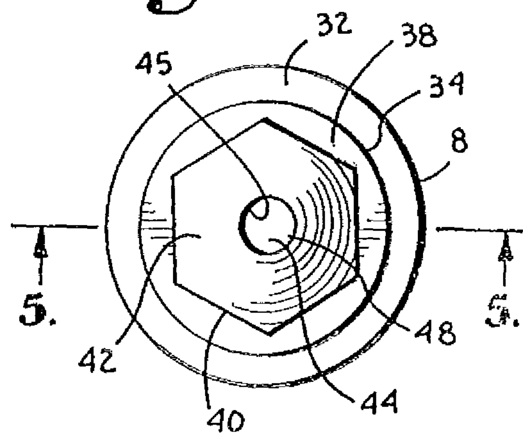
FIG. 4 is an enlarged top plan view of the shank of FIG. 1.

The retainer structure or ring 12 is used to retain the capture structure 8 of the shank 4 within the head 10. The retainer structure 12, best illustrated by FIGS. 1-3 and 6-8, has an operational central axis that is the same as the elongate axis A associated with the shank 4, but when the retainer structure 12 is separated from the shank 4, the axis of rotation is identified as axis C, as shown in FIG. 3. The retainer structure 12 has a central bore 90 that passes entirely through the retainer structure 12 from a top surface 92 to a bottom surface 94 thereof. A first inner cylindrical surface 96 defines a substantial portion of the bore 90, the surface 96 having a helically wound advancement structure thereon as shown by a helical rib or thread 98 extending from adjacent the bottom surface 94 to adjacent a flat, seating surface 99 disposed perpendicular to the inner surface 96.

Although a simple helical rib 98 is shown in the drawings, it is foreseen that other helical structures including other types of threads, such as buttress and reverse angle threads, and non threads, such as helically wound flanges with interlocking surfaces, may be alternatively used in an alternative embodiment of the present invention. The inner cylindrical surface 96 with helical rib 98 are configured to mate under rotation with the capture structure outer surface 34 and helical advancement structure or thread 36, as described more fully below.

The retainer structure 12 further includes a second inner wall or cylindrical surface 102, coaxial with the first inner cylindrical surface 96. The surface 102 is disposed between the seating surface 99 and the top surface 92 of the retainer structure 12 and has a diameter greater than that of the cylindrical surface 96. As will be described more fully below, the cylindrical surface 102 in cooperation with the seating surface 99 and the surface 38 of the retainer structure 12, provide a recess about the base of the tool engagement structure 40 and a stable seating surface for the tool 31, as shown in FIG. 9. The wall 102 which is the outer wall of the recess may be shaped to fit an outer surface of the tool 31 and may be faceted or especially hexagonal in shape to better grip the tool 31.

The retainer structure or ring 12 has a radially outer partially spherically shaped surface 104 sized and shaped to mate with the partial spherical shaped seating surface 82 of the head and having a third radius approximately equal to the first radius associated with the surface 82. The retainer structure third radius is larger than the second radius R of the neck 83 of the head 10. Although not required, it is foreseen that the outer partially spherically shaped surface 104 may be a high friction surface such as a knurled surface or the like.

The elongate rod or longitudinal member 21 that is utilized with the assembly 1 can be any of a variety of implants utilized in reconstructive spinal surgery, but is normally a cylindrical elongate structure having a cylindrical surface 106 of uniform diameter and having a generally smooth surface. The rod 21 is preferably sized and shaped to snugly seat near the bottom of the U-shaped channel 56 of the head 10 and, during normal operation, is positioned slightly above the bottom of the channel 56 at the lower seat 58. In particular, the rod 21 normally directly or abutingly engages the shank top surface 42, as shown in FIG. 10 and is biased against the dome shank top surface 42, consequently biasing the shank 4 downwardly in a direction toward the base 50 of the head 10 when the assembly 1 is fully assembled. For this to occur, the shank top surface 42 must extend at least slightly into the space of the channel 56 when the retainer structure 12 is snugly seated in the lower part of the head cavity 80. The shank 4 and retainer structure 12 are thereby locked or held in position relative to the head 10 by the rod 21 firmly pushing downward on the shank top surface 42.

With reference to FIGS. 1, 10 and 11, the closure structure or closure top 18 can be any of a variety of different types of closure structures for use in conjunction with the present invention with suitable mating structure on the upstanding arms 52 and 54. In the embodiment shown, the closure top 18 is rotatably received between the spaced arms 52 and 54.

The illustrated closure top 18 has a generally cylindrical shaped base 108 with an upwardly extending break-off head 110. The base 108 includes a helically wound guide and advancement structure 111 that is sized, shaped and positioned so as to engage and interlock with the guide and advancement structure 62 on the arms 52 and 54 to provide for rotating advancement of the closure structure 18 into the head 10 when rotated clockwise and, in particular, to cover the top or upwardly open portion of the U-shaped channel 56 to capture the rod 21, preferably without splaying of the arms 52 and 54. The closure structure 18 also operably biases against the rod 21 by advancement and applies pressure to the rod 21 under torquing, so that the rod 21 is urged downwardly against the shank top end surface 42 that extends up into the channel 56. Downward biasing of the shank top surface 42 operably produces a frictional engagement between the rod 21 and surface 42 and also urges the retainer structure 12 toward the base 50 of the head 10, so as to frictionally seat the retainer structure external spherical surface 104 fixedly against the partial internal spherical seating surface 82 of the head 10, also fixing the shank 4 and retainer structure 12 in a selected, rigid position relative to the head 10.

In the embodiment shown, the closure structure includes a break-off head 110 secured to the base 108 at a neck 114 that is sized and shaped so as to break away at a preselected torque that is designed to properly seat the retainer structure 12 in the head 10. The break-off head 110 includes an external faceted surface 115 that is sized and shaped to receive a conventional mating socket type head of a driving tool (not shown) to rotate and torque the closure structure 18. The break-off head 110 also includes a central bore 117 and grooves 118 for operably receiving manipulating tools.

The closure structure 18 also includes removal tool engagement structure which in the present embodiment is in the form of a hex-shaped and axially aligned aperture 116 disposed in the base 108, as shown in FIGS. 10 and 11. The hex aperture 116 is accessible after the break-off head 110 breaks away from the base 108. The aperture 116 is coaxial with the helically wound guide and advancement structure 111 and is designed to receive a hex tool, of an Allen wrench type, into the aperture 116 for rotating the closure structure base 108 subsequent to installation so as to provide for removal thereof, if necessary. Although a hex-shaped aperture 116 is shown in the drawings, the tool engagement structure may take a variety of tool-engaging forms and may include one or more apertures of various shapes, such as a pair of spaced apart apertures, or a left hand threaded bore, or an easyout engageable step down bore, or a Torx aperture, or a multi-lobular aperture or the like.

Figure 6:
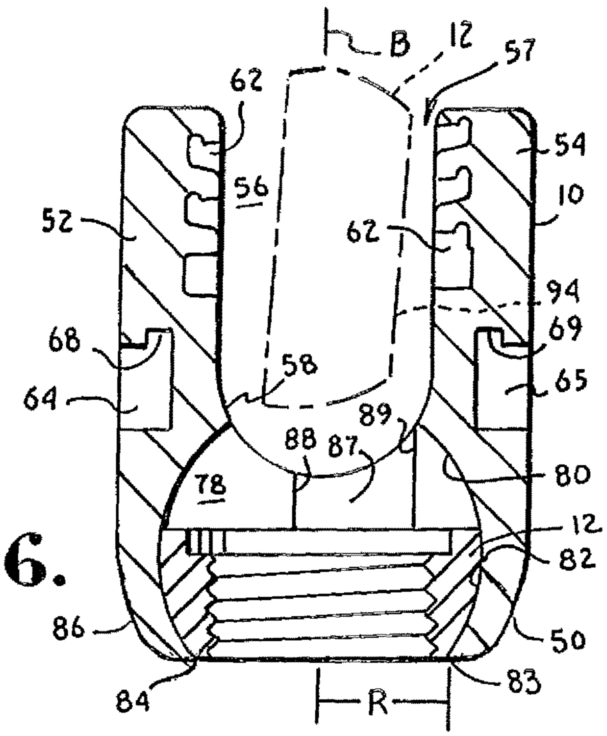
FIG. 6 is an enlarged cross-sectional view of the head, taken along the line 6-6 of FIG. 1, and showing the retainer structure seated in the head (in solid lines) and illustrating the retainer structure being inserted into the head (in dashed lines).

Prior to the polyaxial bone screw assembly 1 being placed in use according to the invention, the ring-like retainer structure 12 is typically first inserted or top-loaded, into the head U-shaped channel 56, as is shown in dotted lines in FIG. 6, and then into the cavity 78 through the vertical loading recess 87 to dispose the structure 12 within the inner surface 80 of the head 10. Then, the retainer structure 12 is rotated approximately 90 degrees so as to be coaxial with the head 10 and then seated in sliding engagement with the seating surface 82 of the head 10, also shown in FIG. 6.

With reference to FIG. 7, the shank capture structure 8 is then inserted or bottom-loaded into the head 10 through the bore 84 defined by the neck 83. The retainer structure 12, now disposed in the head 10 is coaxially aligned with the shank capture structure 8 so that the helical advancement structure 36 rotatingly mates with the helical advancement structure 98 of the retainer structure 12.

The shank 4 and or the retainer structure 12 are rotated to fully mate the structures 36 and 98 along the respective cylindrical surfaces 34 and 96, as shown in FIG. 7, fixing the capture structure 8 to the retainer structure 12, until the seating surface 38 and the seating surface 99 are contiguous and disposed in the same plane and the rim 37 abuts the surface 94 of the retainer structure 12 as shown in FIG. 8. Permanent, rigid engagement of the capture structure 8 to the retainer structure 12 may be further ensured and supported by the use of adhesive, a spot weld, deforming one or both threads with a punch or the like.

As shown in FIG. 8, at this time the shank 4 is in slidable and rotatable engagement with the head 10, while the capture structure 8 and the lower aperture or neck 83 of the head 10 cooperate to maintain the shank body 6 in rotational relation with the head 10. According to the embodiment of the invention shown in FIGS. 1-11, only the retainer structure 12 is in slidable engagement with the head spherical seating surface 82. Both the capture structure 12 and threaded portion of the shank body 6 are in spaced relation with the head 10.

It is believed that an advantage to this embodiment is that, although the shank 6 could engage the head lower aperture or neck 83 when rotated fully relative to the head 10 as best illustrated in FIG. 8, upper shank body 6 does not contact the lower spherical seating surface 82, so that rotational stresses between the capture structure 8 and the retainer structure 12 are lessened, making it less likely that the retainer structure 12 would loosen from the capture structure 8 or that the capture structure would fail or break when the assembly 1 is implanted and loaded.

An extent of rotation is shown in FIG. 8 where it is illustrated that the shank body 6 can be rotated through a substantial angular rotation relative to the head 10, both from side to side and from front to rear so as to substantially provide a universal or ball joint wherein the angle of rotation is only restricted by engagement of the neck 26 of the shank body 6 with the neck or lower aperture 83 of the head 10.

With reference to FIG. 9, the assembly 1 is then typically screwed into a bone, such as the vertebra 15, by rotation of the shank 4 using the driving tool 31 that operably drives and rotates the shank 4 by engagement thereof with the hexagonally shaped extension head 40 of the shank 4. Preferably, when the driving tool 31 engages the head 40, an end portion 118 thereof is disposed in a recess defined by the head 40, the seating surface 38, the contiguous seating surface 99 and the inner cylindrical surface 102, with a bottom surface 119 of the tool 31 contacting and frictionally engaging both the seating surface 38 and the seating surface 99. Some frictional engagement between an outer surface 120 of the tool 31 with the cylindrical surface 102 may also be achievable during rotation of the driving tool 31.

It is foreseen that in other embodiments according to the invention, the tool engaging recess may be defined by only one of the seating surface 38 or the seating surface 99. For example, a retainer structure might not include a seating surface, so a driving tool might seat or mate only with a seating surface or an internal aperture of a shank capture structure. Alternatively, the tool engaging end of a capture structure might be of a size and shape that a driving tool substantially seats on a seating surface of a retainer structure or ring and not the capture structure.

Typically, the head 10 and the retainer structure 12 are assembled on the shank 4 before inserting the shank body 6 into the vertebra 15, but in certain circumstances, the shank body 6 can be first partially implanted in the bone with the capture structure 8 extending proud to allow assembly with the head 10 utilizing the retainer structure 12. Then the shank body 6 can be further driven into the vertebra 15.

With reference to FIGS. 1 and 5 as well as FIG. 9, the vertebra 15 may be pre-drilled to minimize stressing the bone and have a guide wire (not shown) that is shaped for the cannula 44 inserted to provide a guide for the placement and angle of the shank 4 with respect to the vertebra 15. A further tap hole may be made using a tap with the guide wire as a guide. Then, the assembly 1 or the solitary shank 4, is threaded onto the guide wire utilizing the cannulation bore 44 by first threading the wire into the bottom opening 46 and then out of the top opening 48. The shank 4 is then driven into the vertebra 15, using the wire as a placement guide.

With reference to FIGS. 1, 10 and 11, the rod 21 is eventually positioned within the head U-shaped channel 56, and the closure structure or top 18 is then inserted into and advanced between the arms 52 and 54 so as to bias or push against the rod 21. The break-off head 110 of the closure structure 18 is twisted to a preselected torque, for example 90 to 120 inch pounds, to urge the rod 21 downwardly. The shank top end surface 42, because it is rounded to approximately equally extend upward into the channel 56 approximately the same amount no matter what degree of rotation exists between the shank 4 and head 10 and because the surface 42 is sized to extend upwardly into the U-shaped channel 56, the surface 42 is engaged by the rod 21 and pushed downwardly toward the base 50 of the head 10 when the closure structure 18 biases downwardly toward and onto the rod 21. The downward pressure on the shank 4 in turn urges the retainer structure 12 downward toward the head seating surface 82, with the retainer structure seating surface 99 in frictional engagement with the head seating surface 82. As the closure structure 18 presses against the rod 21, the rod 21 presses against the shank and the retainer structure 12 that is now rigidly attached to the shank 4 which in turn becomes frictionally and rigidly attached to the head 10, fixing the shank body 6 in a desired angular configuration with respect to the head 10 and rod 21.

FIG. 10 illustrates the polyaxial bone screw assembly 1 and including the rod 21 and the closure structure 18 positioned in a vertebra 15. The axis A of the bone shank 4 is illustrated as not being coaxial with the axis B of the head 10 and the shank 4 is fixed in this angular locked configuration. Other angular configurations can be achieved, as required during installation surgery due to positioning of the rod 21 or the like.

If removal of the assembly 1 and associated rod 21 and closure structure 18 is necessary, disassembly is accomplished by using a driving tool of an Allen wrench type (not shown) mating with the aperture 116 and turned counterclockwise to rotate the base 108 and reverse the advancement thereof in the head 10. Then, disassembly of the assembly 1 is accomplished in reverse order to the procedure described previously herein for assembly.

Figure 12:
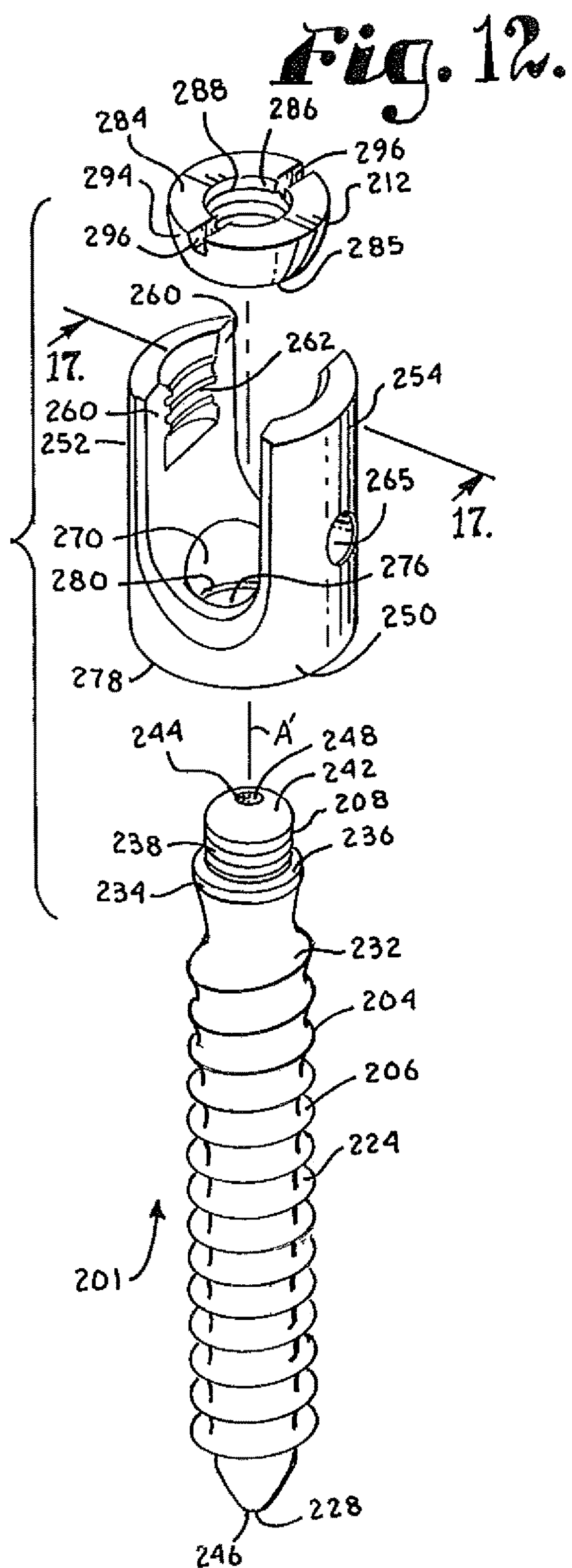
FIG. 12 is an exploded perspective view of an alternative embodiment of a polyaxial bone screw assembly according to the present invention having a shank with an upper capture structure, a head, and a closed ring-like retainer structure.

With reference to FIGS. 12-25, the reference number 201 generally represents a second or alternative embodiment of a polyaxial bone screw apparatus or assembly according to the present invention. As shown in FIG. 12, the assembly 201 includes a shank 204 that has a body 206 integral with a capture structure 208, a head 210, and a retainer structure 212. The shank 204, head 210 and retainer structure 212 are typically assembled prior to implantation of the shank body 206 into a vertebra 215, as shown in FIGS. 18-22.

Figures 22, 23:
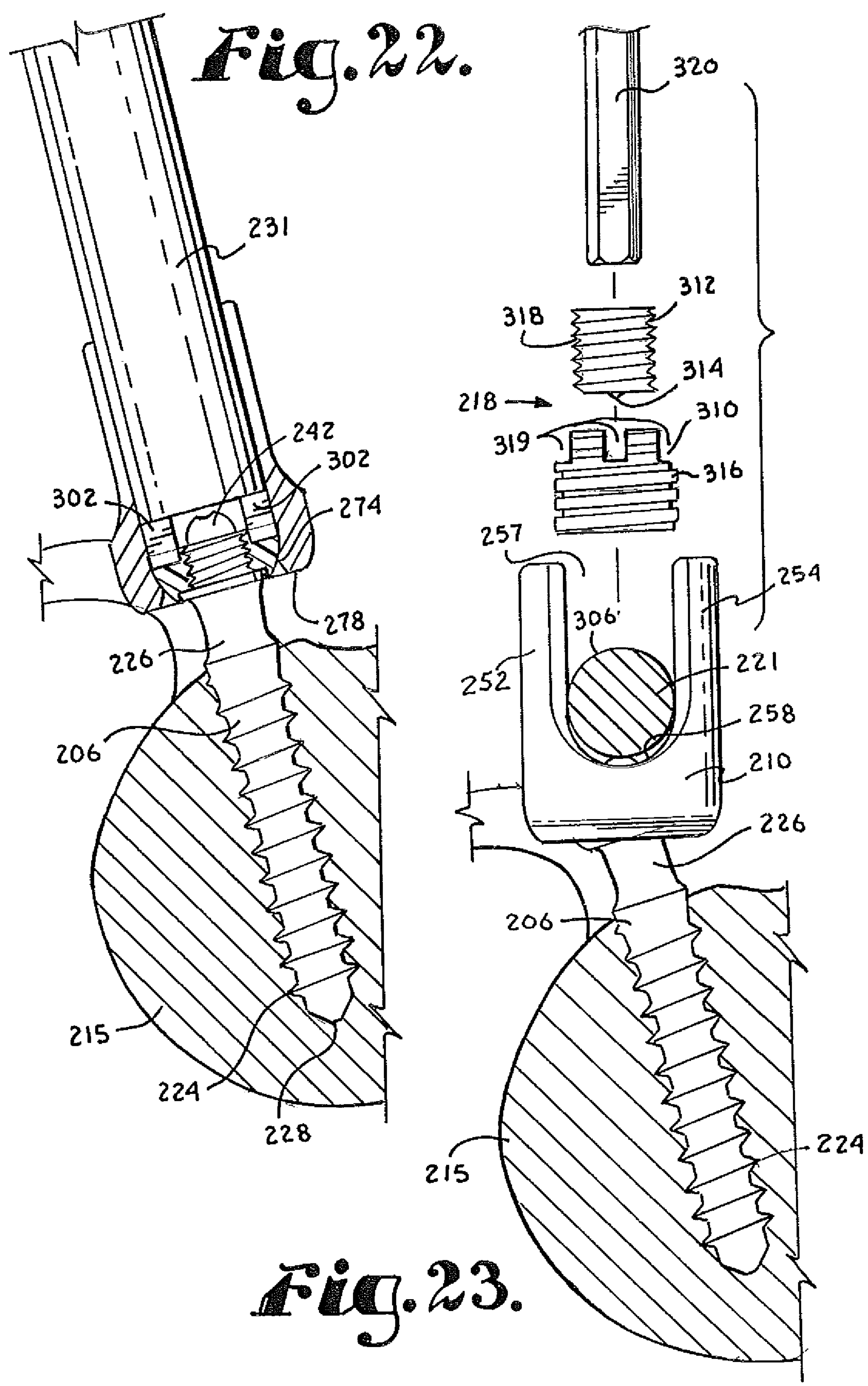
FIG. 22 is an enlarged cross-sectional view of a vertebra, and the head and retainer structure of FIG. 12, showing the shank being implanted into the vertebra using a driving tool mounted on the shank capture structure and the retainer structure.
FIG. 23 is an exploded fragmentary, partially cross-sectional view of the embodiment of FIG. 12, showing a rod in contact with the domed upper extension of the capture structure and illustrating a two-piece closure member structure and driving tool for biasing the rod against the domed upper extension of the capture structure.

FIG. 23 further shows a closure assembly 218 of the invention for biasing a longitudinal member such as a rod 221 against the capture structure 208 so as to fix the rod 221 relative to the vertebra 215.

Similar to the embodiment shown in FIGS. 1-11, the alternative embodiment of the invention 201 provides for the head 210 and shank 204 to cooperate in such a manner that the head 210 and shank 204 can be secured at any of a plurality of obtuse angles, relative to one another and within a selected range of angles both side to side and front to rear, to enable flexible engagement of the assembly 201 with the rod 221, as shown in FIG. 19, and will be described in more detail below. That is the two elements, the head 210 and the shank 204, are articulatable or rotatable relative to each other within a preselected range of movement until locked in a fixed configuration at the end of the procedure.

The shank 204, best illustrated in FIGS. 12 and 16 is elongate, with the shank body 206 having a helically wound bone implantable thread 224 extending from near a neck 226 located adjacent to the capture structure 208 to a tip 228 of the body 206 and extending radially outward therefrom. During use, the body 206 utilizing the thread 224 is implanted into the vertebra 215 leading with the tip 228 and driven down into the bone with an installation tool 231 to adjacent the neck 226 as shown in FIG. 22, described more fully in the paragraphs below. The shank 204 has an elongate axis of rotation generally identified by the reference letter A'.

The neck 226 extends axially outward and upward from the shank body 206. The neck 226 constricts to a reduced radius as compared to an adjacent top 232 of the body 206. Further extending axially and outwardly from the neck 226 is the capture structure 208 that provides a connective or capture apparatus disposed at a distance from the shank body top 232 and thus at a distance from the vertebra 215 when the body 206 is implanted in the vertebra 215. The capture structure 208 is configured for connecting the shank 204 with the head 210 and the retainer structure 212.

The capture structure 208 includes an outer substantially cylindrical surface 234 contiguous to the neck 226 and coaxial with the shank body 206. The cylindrical surface 234 is also contiguous and disposed substantially perpendicular to a seating surface 236. The seating surface 236 is also coaxial with the shank body 206 and the cylindrical surface 234. Both the cylindrical surface 234 and the seating surface 236 are configured to come into frictional engagement with the retainer structure 212, as described more fully below.

Perpendicular to and contiguous with the seating surface 236 is a second cylindrical surface 238 having a helically wound advancement structure thereon as shown by a helical rib or thread 240 extending from adjacent the seating surface 236 to adjacent a rod engagement dome 242. Although a simple helical rib 240 is shown in the drawings, it is foreseen that other helical structures including other types of threads, such as buttress and reverse angle threads, and non threads, such as helically wound flanges with interlocking surfaces, may be alternatively used in an alternative embodiment of the present invention.

The top end surface or dome 242 of the shank 204 is preferably convex, domed or curved as shown in the drawings, and sized and positioned for positive engagement with the rod 221 when the bone screw assembly 201 is assembled, as shown in FIGS. 24 and 25. If desired, the dome 242 may be scored or knurled. In certain embodiments, the purpose of the dome 242 is simply to be engaged by the rod 221 during assembly and be biased downwardly in such a manner as to frictionally engage the retainer structure 212, which is secured to the shank 206 at this time, within the head 210, as described below. The dome 242 may be radiused so that the dome 242 engages the rod 221 at generally the same level or height relative to the head channel lower surface 258, even as the head 210 is swivelled relative to the shank 204. However in other embodiments the dome 242 can have other shapes.

In the embodiment shown in FIGS. 12-25, the shank body 206 and capture structure 208 components are integral. Furthermore the shank 204 is cannulated, having a small cylindrical central bore 244 extending an entire length of the shank 204 along the axis A'. The bore 244 is defined by an inner cylindrical wall 245 of the shank 204 and has a first circular opening 246 at the shank tip 228 and a second circular opening 248 at the dome top surface 242. The bore 244 is coaxial with the threaded body 206 and capture structure outer cylindrical surfaces 234 and 238. The bore 244 provides a passage through the shank 204 interior for a length of wire (not shown) inserted into the vertebra 215 prior to the insertion of the shank body 206, the wire providing a guide for accurate insertion of the shank body 206 into the vertebra 215.

Referring to FIGS. 12, 17 and 18, the head 210 is substantially cylindrical in external profile and includes a base portion 250 integral with a pair of upstanding arms 252 and 254 forming a U-shaped channel 256 between the arms 252 and 254 with an upper opening 257 and the lower surface 258 having substantially the same radius as the rod 221. In operation, the rod 221 preferably is located just above the channel lower surface 258.

Each of the arms 252 and 254 has an interior surface 260 that defines an inner cylindrical profile and includes a partial helically wound guide and advancement structure 262. Similar to the guide and advancement structure 62 shown with respect to FIGS. 1-11, the guide and advancement structure 262 is a partial helically wound flangeform configured to mate and interlock under rotation about an axis B' with a similar structure disposed on the closure top assembly 218, as described more fully below. However, it is foreseen that the guide and advancement structure 262 could alternatively be a V-shaped thread, a buttress thread, a reverse angle thread or other thread like or non-thread like helically wound advancement structures for operably guiding under rotation and advancing the closure top between the arms 252 and 254. Also, it is foreseen that this mating advancement structure could be located on the cylindrical external surfaces of the arms 252 and 254.

The head 210 includes external, closed end grip bores 264 and 265 disposed on the respective arms 252 and 254 for positive engagement by a holding tool (not shown) to facilitate secure gripping of the head 210 during assembly of the head 210 with the shank 204 and retainer structure 212. Furthermore, the grip bores 264 and 265 may be utilized to hold the head 210 during the implantation of the shank body 206 into the vertebra 215. The bores 264 and 265 are centrally located on the respective arms 252 and 254. However, it is noted that the bores 264 and 265 may be configured to be of a variety of sizes and locations along outer surfaces of the arms 252 and 254.

Communicating with the U-shaped channel 256 of the head 210 is a chamber or cavity 268 substantially defined by an inner surface 270 of the base 50, the cavity 268 opening upwardly into the U-shaped channel 256. The inner surface 270 is substantially spherical, with at least a portion thereof forming a partial internal spherical seating surface 272 having a first radius, the surface 272 for mating with the retainer structure 212, as described more fully below.

The base 250 further includes a restrictive aperture, opening or neck 274, having a second radius R' and partially defining a bore 276 communicating with the cavity 268 and a bottom exterior 278 of the base 50. The bore 276 is coaxial with a rotational axis B' of the head 210. A bevel 280 extends between the neck 274 and the bottom exterior 278. The neck 274 and associated bore 276 are sized and shaped to be smaller than a radial dimension of the retainer structure 212, as will be discussed further below, so as to form a restriction at the location of the neck 274 relative to the retainer structure 212, to prevent the structure 212 from passing between the cavity 268 and the bottom exterior 278 of the head 210, when fully seated. The bevel 280 widens the angular range of the shank 204 when assembled with the head 210.

The retainer structure or ring 212 is used to retain the capture structure 208 of the shank 204 within the head 210. The retainer structure 212, best illustrated by FIGS. 12-14, has an operational central axis that is the same as the elongate axis A' associated with the shank 204, but when the retainer structure 212 is separated from the shank 204, the axis of rotation is identified as axis C', as shown in FIG. 14. The retainer structure 212 has a central bore 282 that passes entirely through the retainer structure 212 from a top surface 284 to a bottom surface 285 thereof. A first inner cylindrical surface 286 defines a substantial portion of the bore 282, the surface 286 having a helically wound advancement structure thereon as shown by a helical rib or thread 288 extending from adjacent the top surface 284 to adjacent a seating surface 290 disposed perpendicular to the inner surface 286.

Although a simple helical rib 288 is shown in the drawings, it is foreseen that other helical structures including other types of threads, such as buttress and reverse angle threads, and non threads, such as helically wound flanges with interlocking surfaces, may be alternatively used in an alternative embodiment of the present embodiment. The first inner cylindrical surface 286 with helical rib 288 are configured to mate under rotation with the capture structure outer surface 238 and helical advancement structure or thread 240, as described more fully below.

The retainer structure 212 further includes a second inner cylindrical surface 292, coaxial with the first inner cylindrical surface 286. The surface 292 is disposed between the seating surface 290 and the bottom surface 285 of the retainer structure 212 and has a diameter greater than that of the cylindrical surface 286. As will be described more fully below, the cylindrical surface 292 in cooperation with the seating surface 290, provide a recess for insertion of the shank 204 thereinto and the seating surface 290 provides a frictional contact or seating surface for the seating surface 236 of the capture structure 108 as shown in FIGS. 18 and 19.

The retainer structure or ring 212 has a radially outer partially spherically shaped surface 294 sized and shaped to mate with the partial spherical shaped seating surface 272 of the head and having a third radius approximately equal to the first radius associated with the surface 272. The retainer structure third radius is larger than the second radius R' of the restrictive neck 274 of the head 210.

Figure 13:
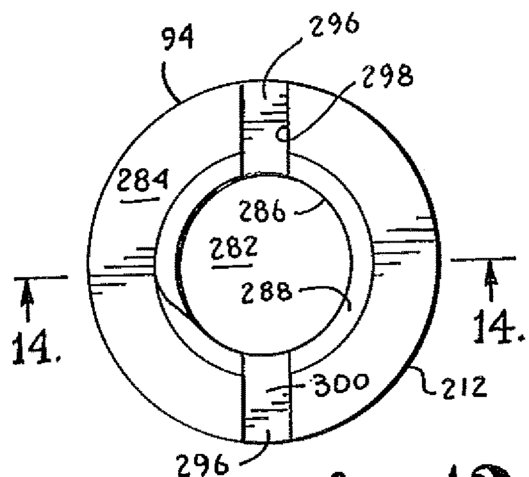
FIG. 13 is an enlarged top plan view of the retainer structure of FIG. 12.
Figure 14:
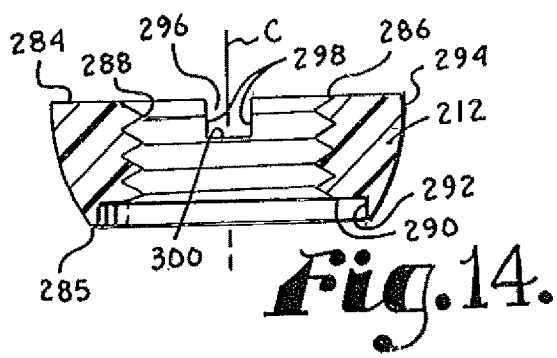
FIG. 14 is an enlarged cross-sectional view of the retainer structure of FIG. 13, taken along line 14-14 of FIG. 13.
Figure 15:
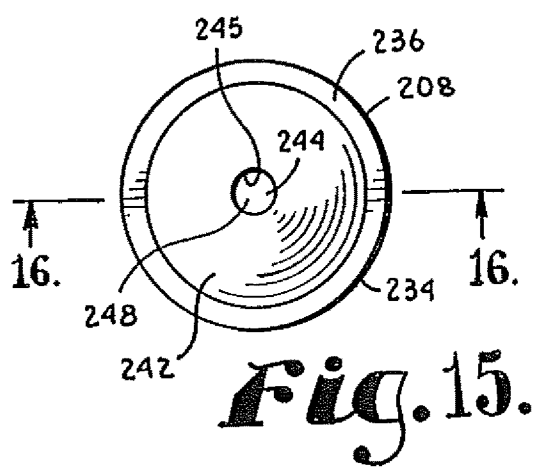
FIG. 15 is an enlarged top plan view of the shank of FIG. 12.

The retainer structure 212 shown in FIG. 13 further includes a transverse slot 296 formed in the top surface 284 thereof for engagement of the driving tool 231 shown in FIG. 22. It is foreseen that a retainer structure according to the present invention may include two or more slots in the retainer top surface, or other types of apertures for engaging with a cooperating driving tool. The slot 296 is defined by a pair of spaced, parallel walls 298 perpendicular to a base 300. The slot 296 extends out to the outer spherical surface 294 from each side of the central bore 282. A plane aligned with the center of the slot 296 intersects the rotational axis C'. The tool 231 includes a pair of spaced slot engaging extensions 302 sized and shaped to seat in the slot 296 on either side of the central bore 282 and with the region therebetween configured to clear the rod-engagement dome 242 during assembly and while driving and rotating the shank body 206 into the vertebra 215.

With reference to FIGS. 20 and 21, the slot 296 is preferably sized such that, after the shank 204, head 210 and retainer structure 12 have been assembled, a tool such as the illustrated punch 304 may be inserted into the slot 296 to deform the helical rib 240 of the capture structure 208 by causing a nick or deformity 305 thereon, thereby preventing relative rotation therebetween and rigidly fixing the rib 240 against the helical rib 288 of the retainer structure 212, ensuring a fixed relation between the shank capture structure 208 and the retainer structure 212.

The elongate rod or longitudinal member 221 that is utilized with the assembly 201 can be any of a variety of implants utilized in reconstructive spinal surgery, but is normally a cylindrical elongate structure having a cylindrical surface 306 of uniform diameter. The rod 221 is preferably sized and shaped to snugly seat at the lower channel seat 258 near the bottom of the U-shaped channel 256 of the head 210, and, during normal operation, is positioned slightly above the bottom of the channel 256. In particular, the rod 221 normally engages the shank top surface or dome 242, as shown in FIG. 24 and is biased against the dome 242, consequently biasing the shank 204 downwardly in a direction toward the base 250 of the head 210 when the assembly 201 is fully assembled.

With reference to FIGS. 23-25, the closure or top assembly 218 can be any of a variety of different types of closure structures for use in conjunction with the present invention with suitable mating structure internally or externally on the upstanding arms 252 and 254. The illustrated closure top assembly 218 includes a cylindrical closure plug 310 and a cylindrical inner set screw or plug 312. The inner plug 312 includes a pointed rod engaging projection or point 314 at a bottom surface thereof and a tool engagement aperture 315 disposed in an opposite or top surface thereof, illustrated in FIGS. 24 and 25 as a hex aperture. However, the tool engagement structure 315 may take a variety of tool-engaging forms and may include more than one aperture, such as a pair of spaced apertures or other shapes such as Torx or the like.

The closure plug 310 includes an outer helically wound guide and advancement structure 316 that is sized, shaped and positioned so as to engage the guide and advancement structure 262 on the arms 252 and 254 to provide for the rotation of the closure plug 310 into the head 210 and, in particular, to enclose the top of the U-shaped channel 56 to capture the rod 221, preferably without splaying of the arms 252 and 254. The closure plug 310 is a hollow cylinder and also includes an inner threaded cylindrical wall 317 sized and shaped to receive and rotatingly mate with an outer threaded surface 318 of the inner plug or set screw 312. As shown in FIG. 25, the closure plug 310 further includes a pair of transverse slots 319 in perpendicular relation, the slots 319 for engagement with a driving tool (not shown). The hex aperture 315, closure plug inner wall 317, inner plug wall 318, and arms 252 and 254 are configured so as to be coaxial upon assembly. A hex driving tool 320 can be inserted into the aperture 315 of the inner plug 312 to drive and rotate both the inner plug 312 into the closure plug 310 and the closure plug 310 into the head arms 252 and 254. Preferably, the closure plug 310 is first driven and rotated into the arms 252 and 254 by engaging a tool with the slots 319, followed by the inner plug 312 being rotated individually into the closure plug 312 by engagement with the tool 320.

The closure assembly 218 operably biases against the rod 221, with the projection 314 frictionally engaging and abrading the rod surface 306 and thereby applying pressure to the rod 221 under torquing, so that the rod 221 is urged downwardly against the rod-engagement dome 242. Downward biasing of the dome 242 operably produces a frictional engagement between the rod 221 and the dome 242 and also urges the retainer structure 212 toward the base 250 of the head 210, so as to frictionally seat the retainer structure external spherical surface 294 fixedly or in a locked configuration against the partial internal spherical seating surface 272 of the head 210, also fixing the shank 204 and retainer structure 212 in a selected, rigid angular position relative to the head 210.

If necessary, the hex tool 320 may be used to loosen the assembly subsequent to installation, and for removal of the plugs 310 and 312.

When the polyaxial bone screw assembly 201 is placed in use according to the invention, the closed ring-like retainer structure 212 is typically first inserted or top-loaded, into the head U-shaped channel 256 and then into the cavity 268 within the inner surface 270 of the head 210. Although not shown, the inner surface 270 may include a loading recess similar to the recess 87 disclosed with respect to the first embodiment assembly 1, and may be loaded into the head 210 in similar fashion. The retainer structure 212 is then seated with the surface 294 in sliding engagement with the spherical seating surface 272 of the head 210, as shown in FIG. 17. Although not required, both the retainer structure and head surfaces 294 and 272, respectively may be high friction surfaces, such as knurled surfaces, or the like.

With reference to FIGS. 17 and 18, the shank capture structure 208 is inserted or bottom-loaded into the head 210 through the bore 276 defined by the neck 274. The retainer structure 212, now disposed in the head 210 is coaxially aligned with the shank capture structure 208 so that the helical advancement structure 240 of the capture structure 208 rotatingly mates with the helical advancement structure 288 of the retainer structure 212. The shank 204 and or the retainer structure 212 are rotated to fully mate the structures 240 and 288 along the respective cylindrical surfaces 238 and 286, as shown in FIG. 18, securing or fixing the capture structure 208 to the retainer structure 212, until the seating surface 236 and the seating surface 290 are in frictional contact, as shown in FIG. 19.

With reference to FIGS. 20 and 21, permanent, fixed or rigid engagement of the capture structure 208 to the retainer structure 212 may be further enhanced by deforming the helical advancement structure or thread 240 by inserting the pointed tool 304 into the slot 296 and marring or nicking the helical rib 240 with the tool 304, resulting in the nick or deformity 305, as is shown in FIG. 21. The deformity 305 causes the rib 240 to abut against the helical rib 288 of the retainer structure 212, thereby resisting unscrewing and ensuring a fixed relation between the shank capture structure 208 and the retainer structure 212. As with the assembly 1, the fixed relation between the rib 240 and the rib 288 may also be accomplished by the use of an adhesive, or spot weld or the like, in any area of the retainer structure cylindrical surface 238, especially where exposed by the slot 296.

As shown in FIG. 19, the shank 204 with integral capture structure 208 and attached retainer structure 212 are in pivotable engagement with the head 210. The capture structure 208 and the neck 274 of the head 210, connecting the shank 204 to the head 210 and after locking the retainer structure 212 keeping the shank body 206 in fixed rotational relation with the head 210.

According to the embodiment of the invention shown in FIGS. 12-25, only the retainer structure 212 is in slidable engagement with the head spherical seating surface 272. The capture structure 208 and threaded portion of the shank body 206 are in spaced relation with the head 210, although the shank outer neck 226 could engage the head restrictive neck 274 at a full rotation, as best illustrated in FIG. 24.

An extent of rotation is shown in FIG. 19 in phantom lines where it is illustrated that the shank body 206 can be rotated through a substantial angular rotation relative to the head 210, both from side to side and from front to rear so as to substantially provide a universal or ball joint wherein the angle of rotation is only restricted by engagement of the neck 226 of the shank body 206 with the neck 274 of the head 210.

With reference to FIG. 22, the assembly 201 is then typically screwed into a bone, such as the vertebra 215, by rotation of the shank 204 using the driving tool 231 that operably drives and rotates the shank 204 by engagement thereof with the transverse slot 296 of the retainer structure 212. Preferably, when the driving tool 231 engages the retainer structure 212, each of the tool prong like extensions 302 are disposed in a recess defined by the slot walls 298 and the base of the slot 300, with the tool extensions 302 seated upon and driving against the slot base 300.

The head 210 and the retainer structure 212 are assembled on the shank 204 before inserting the shank body 206 into the vertebra 215. With reference to FIG. 16 and FIG. 22, the vertebra 215 may be pre-drilled to minimize stressing the bone, as well as the connection between the retainer ring and capture structure, and a guide wire inserted to provide a guide for the placement and angle of the shank 204 with respect to the vertebra 215 (not shown). A bone screw shaped tap hole may be made utilizing a tap. Then, the assembly 201 or the solitary shank 204, is threaded onto the guide wire utilizing the cannulation bore 244 by first threading the wire into the bottom opening 246 and then out of the top opening 248. The shank 204 is then driven into the vertebra 215, using the wire as a screw placement guide and the wire is then removed.

With reference to FIGS. 23-25, the rod 221 is eventually positioned within the head U-shaped channel 256, and the closure assembly 218 is then inserted into and advanced between the arms 252 and 254 so as to bias or push against the rod 221. Specifically, a driving tool (not shown, but could be the same tool 231 shown in FIG. 22) is inserted into the slots 319 of the closure plug 310 to drive and rotate the closure plug 310 into the head arms 252 and 254. Subsequently, the hex driving tool 320 is inserted into the aperture 315 of the inner plug 312 to drive and rotate the inner plug 312 into the closure plug 310.

The shank top end surface or dome 242, because it is rounded and sized to extend upwardly into the U-shaped channel 256, is engaged by the rod 221 and pushed downwardly toward the base 250 of the head 210 when the outer closure structure and inner plug projection 314 bias downwardly toward and onto the rod 221. The downward pressure on the shank 204 in turn urges the retainer structure 212 downward toward the head seating surface 272, with the retainer structure seating surface 294 into frictional engagement with the head seating surface 272. As the outer plug and inner set screw 312 press against the rod 221, the rod 221 presses against the shank and rigidly attached retainer structure 212, which in turn becomes rigidly and frictionally attached to the head 210, fixing the shank body 206 in a desired angle with respect to the head 210 and rod 221.

FIGS. 24 and 25 illustrate the polyaxial bone screw assembly 201, the rod 221 and the closure assembly 218 positioned in the vertebra 215. The axis A' of the bone shank 204 is illustrated as not being coaxial with the axis B' of the head 210 and the shank 204 is fixed in this angular locked configuration. Other angular configurations can be achieved, as required during installation surgery due to positioning of the rod 221 or the like.

If removal of the assembly 201 and associated rod 221 and closure assembly 218 is necessary, disassembly is accomplished by using the driving tool 320 mating with the aperture 315 to rotate the inner plug or set screw 312 and reverse the advancement thereof in the outer closure plug 310. Subsequently, the outer plug 310 is loosened by mating the slots 319 with a driver (not shown) to reverse the advancement of the plug 310 in the arms 252 and 254. It may be possible to loosen both the inner plug 312 and the closure plug 310 with the tool 320, thus loosening the closure plug 310 from the head arms 252 and 254, as the outer plug 310 and inner plug 312 may be joined together by threads at the lower ends thereof becoming deformed by engagement with the rod 221. Then, disassembly of the assembly 1 is accomplished in reverse order to the procedure described previously herein for assembly. For disassembly, it is preferred that the retaining structure 312 be strongly secured to the shank 310 by deformation of the threads 238 and 288 or by other locking structure such as welding or pins so that both are assured of being removed as a single unit.

It is to be understood that while certain forms of the present invention have been illustrated and described herein, it is not to be limited to the specific forms or arrangement of parts described and shown.

What is claimed and desired to be secured by Letters Patent is as follows:

1. A pivotal bone anchor assembly configured for surgical implantation, the pivotal bone anchor assembly comprising:

a separate shank and a head, the head having a pair of upstanding arms each with a top surface and an outer surface portion extending toward a bottom of the head, the arms forming a channel configured for receiving a rod and a closure mechanism for closing the channel and locking the rod between the arms, the arms having an internal surface with a discontinuous helically wound guide and advancement structure, the closure mechanism being configured as a one-part closure or two-part closure, the closure mechanism comprising:

a plug body formed in a cylindrical shape with an external surface having a continuous helically wound guide and advancement structure portion formed thereon, the plug body having a longitudinal axis with a first axial opening extending into the plug body from a top surface of the plug body, at least a portion of the first axial opening being closed around an entire perimeter thereof, and the plug body having a bottom surface and a rod engaging projection extending downwardly beyond the bottom surface and axially beneath the first axial opening, the rod engaging projection configured to engage the rod;

wherein, when the closure mechanism is configured as a two-part closure:

the plug body includes an outer plug body configured as a closed ring and the first axial opening is configured as a central bore extending from the top surface to the bottom surface of the outer plug body, the central bore being threaded, the outer plug body further comprises a plurality of spaced apart non-threaded drive structures having axially extending planar surfaces formed in an upper portion of the outer plug body, each drive structure intersecting the central bore and having a lower surface that does not communicate with the bottom surface of the outer plug body; and the two-part closure further comprising a separate inner plug having a longitudinal axis and an outer surface that is configured to be threadedly received in the central bore of the outer plug body, the inner plug having a lower portion that has a solid cross section with a substantially flat bottom surface configured to engage and lock the rod when positioned within the channel, wherein the inner plug includes a single drive structure formed therein and defining a second axial opening that is non-threaded with opposed sides, the single drive structure extending from a top surface of the inner plug to a lower tool abutment surface therein, the lower tool abutment surface located substantially nearer the bottom surface of the inner plug than the top surface of the inner plug, wherein the inner plug is configured to be threadedly received in the outer plug body prior to the two-part closure being received in the channel formed between the upstanding arms of the head, and wherein the helically wound guide and advancement structure portions of the plug body of the one-part closure and the two-part closure are configured to be interchangeable with each other for closing the channel and locking the rod between the arms with the closure mechanism.

2. The assembly according to claim 1, wherein the bottom surface of the inner plug comprises a central point.

3. The assembly according to claim 1, wherein the top surface of the inner plug is flat.

4. The assembly according to claim 1, wherein a thread on the outer surface of the inner plug is continuous from the top surface to the bottom surface of the inner plug.

5. The assembly according to claim 4, wherein the thread on the outer surface of the inner plug is a v-shaped thread.

6. The assembly according to claim 1, wherein the plurality of spaced apart non-threaded drive structures of the outer plug body includes a first radially located slot formed in the top surface of the outer plug body which extends from the external surface to the central bore and intersects the threaded central bore of the outer plug body.

7. The assembly according to claim 6, wherein the plurality of spaced apart non-threaded drive structures of the outer plug body includes a second radially located slot formed in the top surface of the outer plug body diametrically opposed to the first slot which extends from the external surface to the central bore and intersects the central bore.

8. The assembly according to claim 1, wherein the single drive structure of the inner plug has a cross-section with multiple drive surfaces aligned axially about the longitudinal axis of the inner plug.

9. The assembly according to claim 1, wherein the outer plug body with the central bore and inner plug of the two-part closure are configured to be positioned between the upstanding arms of the head and configured so as to not extend above the top surfaces of each of the pair of upstanding arms thereof when the rod is locked between the arms by the two-part closure.

10. The assembly according to claim 1, wherein the inner plug is configured to be threadedly received into the central bore formed in the outer plug body from one of the top surface and the bottom surface of the outer plug body.

11. The assembly according to claim 1, wherein the inner plug is configured to be separately removable from the central bore of the outer plug body after the two-part closure locks the assembly.

12. The assembly according to claim 1, wherein the head includes a lower internal spherical seating surface adjacent a bottom opening in the head so as to provide pivotal movement for the separate shank with respect to the head.

13. The assembly according to claim 1, wherein the helically wound guide and advancement structure portion on the plug body is configured as a buttress thread.

14. The assembly according to claim 1, wherein the single drive structure is configured to non-threadably receive a non-slip driving tool.

15. The assembly according to claim 1, wherein the closure mechanism is configured to not extend past a plane adjacent to and parallel with the top surface on each of the upstanding arms.

16. The assembly according claim 1, wherein the first axial opening of the plug body of the one-part closure is configured as a drive structure having a centrally open non-threaded internal aperture with opposed sides, the sides extending from the top surface of the plug body to a lower tool abutment surface, the lower tool abutment surface spaced a distance above the bottom surface on the plug body of the one-part closure, the bottom surface being configured to engage the rod.

17. A polyaxial bone screw assembly configured for surgical implantation comprising:

a) a shank for attachment to a patient bone;

b) a head separate from the shank having a pair of upstanding arms each with a top surface and an outer surface adjacent the top surface extending toward a bottom of the head, the upstanding arms forming a channel configured for receiving a rod, the upstanding arms having an inner surface with a discontinuous helically wound guide and advancement structure;

c) a closure configured for closing the channel between the upstanding arms, the closure comprising:

i) an outer plug configured as a body with a generally cylindrical shape having at least a lower portion with a continuous external surface including outer threads and a central threaded through-bore with inner threads extending from a top surface to a bottom surface of the body of the outer plug, the body further including a plurality of spaced apart, radially oriented slots having opposed planar surfaces contiguous with the top surface thereof, each slot extending entirely through at least one thread of the outer threads and inner threads;

ii) an inner plug having an outer surface configured to be threadedly received in the central threaded through-bore of the plug body of the outer plug, the inner plug having a longitudinal axis and a central internal aperture communicating with only a top surface thereof, the central internal aperture extending from the top surface to a lower tool abutment surface therein, a bottom most portion of the lower tool abutment surface being located nearer a bottom surface of the inner plug than the top surface thereof, the bottom surface of the inner plug being substantially flat and engageable with the rod, and wherein both the outer plug and the inner plug are configured to be simultaneously positioned together between the upstanding arms of the head when the rod is locked between the arms by the closure.

18. The assembly according to claim 17, wherein the shank is cannulated along an entire length thereof.

19. The assembly according to claim 17, wherein the central internal aperture of the inner plug comprises a multi-surface non-slip internal tool engagement structure.

20. The assembly according to claim 17, wherein the shank includes a retainer engageable with an upper end of the shank configured to hold the shank in the head.

21. The assembly according to claim 20, wherein the rod is configured to remain spaced apart from the retainer when the assembly is in a locked orientation.

22. The assembly according to claim 17, wherein the outer surfaces of the pair of upstanding arms include laterally facing vertically extending sides having planar outwardly facing surfaces parallel with respect to each other.

23. The assembly according to claim 17, wherein the shank includes an upper end capture structure with a drive structure formed in an internal aperture thereof.

24. The assembly according to claim 17, wherein the head has a substantial cylindrical shape.

25. The assembly according to claim 17, wherein the closure is configured to not extend past a plane adjacent to and parallel with the top surface on each of the upstanding arms.

26. A pivotal bone anchor assembly for surgical implantation including a shank and a head having a pair of upstanding arms each with a top surface and laterally facing vertically extending sides having planar outwardly facing surfaces parallel with respect to each other, the arms forming a channel configured for receiving a rod and a two-part closure for closing the channel and locking the rod between the arms, the arms having an internal surface with a discontinuous helically wound guide and advancement structure, the two-part closure comprising:

a) an outer plug body configured as a closed ring with a generally cylindrical shaped external surface having a continuous helically wound guide and advancement structure portion formed thereon, the outer plug body defining a threaded central bore extending from a top surface to a bottom surface of the outer plug body, at least a portion of the outer plug body defining the threaded central bore being circumferentially closed, the outer plug body including a non-threaded drive structure formed in an upper portion of the outer plug body, the drive structure intersecting the threaded central bore;

b) an inner plug having a longitudinal axis and an outer surface that is configured to be threadedly received in the threaded central bore of the outer plug body, the inner plug having a lower portion that has a solid cross section with a bottom surface that is substantially flat and configured to engage and lock the rod when the rod is positioned within the channel, and the inner plug including a drive structure having a non-threaded internal aperture with opposed sides, the non-threaded internal aperture extending from a top surface of the inner plug to a lower tool abutment surface therein, the lower tool abutment surface located substantially nearer the bottom surface of the inner plug than the top surface;

wherein the two-part closure is configured to lock the rod between the arms such that the assembly does not extend over the top surface and any portion of the outer surface on each upstanding arm; and wherein the inner plug is configured to be threadedly receivable in the outer plug body prior to the two-part closure being received in the channel formed between the upstanding arms of the head.

27. The assembly according to claim 26, wherein the non-threaded drive structure of the outer plug body includes a first radially located slot formed in the top surface which extends from the external surface to the threaded central bore and intersects the threaded central bore of the outer plug body.

28. The assembly according to claim 27, wherein the non-threaded drive structure includes a second radially located slot formed in the top surface diametrically opposed to the first radially located slot which extends from the external surface to the threaded central bore and intersects the threaded central bore.

29. A pivotal bone anchor assembly configured for surgical implantation including a separate shank and a head having a pair of upstanding arms each with a top surface and an outer surface extending from adjacent the top surface towards a bottom of the head, the arms forming a channel configured for receiving a rod and a single part closure or a two-part closure for closing the channel and locking the rod between the arms, the arms having an internal surface with a discontinuous helically wound guide and advancement structure, the single part and two-part closure each have an external surface with a continuous helically wound guide and advancement structure configured to mate with the discontinuous helically wound guide and advancement structure, the two-part closure comprising:

a) an outer plug body formed as a closed ring with a generally cylindrical shaped external surface having the continuous helically wound guide and advancement structure formed thereon, the outer plug body defining a threaded central bore extending from a top surface to a bottom surface of the outer plug body, at least a portion of the outer plug body defining the threaded central bore being circumferentially closed, the outer plug body including a plurality of spaced apart non-threaded drive structures having planar surfaces formed in an upper portion of the outer plug body, each drive structure intersecting the threaded central bore and having a lower surface that does not communicate with the bottom surface of the outer plug body; and b) an inner plug having a longitudinal axis and an outer surface that is configured to be threadedly received in the threaded central bore of the outer plug body, the inner plug having a lower portion that has a solid cross section with a bottom surface that is substantially flat and configured to engage and lock the rod when the rod is received within the channel, and the inner plug including a drive structure having a centrally open non-threaded internal aperture with parallel opposed sides, the non-threaded internal aperture extending from a top surface of the inner plug to a lower tool abutment surface therein, the lower tool abutment surface located substantially nearer the bottom surface of the inner plug than the top surface, wherein the inner plug is configured to be threadedly received in the outer plug body prior to the two-part closure being received in the channel formed between the upstanding arms of the head, and the single part closure comprising:

a plug body formed as a generally cylindrical shape having the external surface with the continuous helically wound guide and advancement structure formed thereon, the plug body including a drive structure having a centrally open non-threaded internal aperture with opposed sides, the sides extending from a top surface of the plug body of the single part closure to a lower tool abutment surface therein, the lower tool abutment surface spaced a distance above a bottom surface on the plug body of the single part closure, the bottom surface being configured to engage the rod.

30. The assembly according to claim 29, wherein at least a portion of the outer surface on each arm is planar and parallel with respect to each other.

31. A pivotal bone anchor assembly configured for surgical implantation, the pivotal bone anchor assembly comprising:

a separate shank and a head, the head having a pair of upstanding arms each with a top surface and an outer surface portion extending toward a bottom of the head, the arms forming a channel configured for receiving a rod and a closure mechanism for closing the channel and locking the rod between the arms, the arms having an internal surface with a discontinuous helically wound guide and advancement structure, the closure mechanism being configured as a one-part closure or two-part closure, the closure mechanism comprising:

a plug body formed in a cylindrical shape with an external surface having a continuous helically wound guide and advancement structure portion formed thereon, the plug body having a longitudinal axis with a first axial opening extending from a top surface of the plug body, at least a portion of the first axial opening being closed around an entire perimeter thereof, and the plug body having a bottom surface and a rod engaging projection extending downwardly beyond the bottom surface and axially beneath the first axial opening, the rod engaging projection configured to engage the rod;

wherein, when the closure mechanism is configured as a two-part closure:

the plug body includes an outer plug body configured as a closed ring and the first axial opening is configured as a central bore extending from the top surface to the bottom surface of the outer plug body, the central bore being threaded, the outer plug body further comprises a plurality of spaced apart non-threaded drive structures having axially extending planar surfaces formed in an upper portion of the outer plug body, each drive structure intersecting the central bore and having a lower surface that does not communicate with the bottom surface of the outer plug body; and the two-part closure further comprising a separate inner plug having a longitudinal axis and an outer surface that is configured to be threadedly received in the central bore of the outer plug body, the inner plug having a lower portion that has a solid cross section with a substantially flat bottom surface configured to engage and lock the rod when the rod is positioned within the channel, wherein the inner plug includes a single drive structure formed therein and defining a second axial opening that is non-threaded with opposed sides, the single drive structure of the inner plug extending from a top surface of the inner plug to a lower tool abutment surface therein, the lower tool abutment surface located substantially nearer the bottom surface of the inner plug than the top surface, wherein the inner plug is configured to be threadedly received in the outer plug body prior to the two-part closure being received in the channel formed between the upstanding arms of the head, and wherein the helically wound guide and advancement structure portions on the plug body of the one-part closure and the two-part closure are each configured for closing the channel and locking the rod between the arms with the closure mechanism.

* * * * *